(12) United States Patent
Takahashi et al.

(10) Patent No.: US 12,014,501 B2
(45) Date of Patent: Jun. 18, 2024

(54) IMAGE PROCESSING APPARATUS, MEDICAL IMAGE DIAGNOSTIC APPARATUS, AND BLOOD PRESSURE MONITOR

(71) Applicant: CANON MEDICAL SYSTEMS CORPORATION, Tochigi (JP)

(72) Inventors: Akihito Takahashi, Nasushiobara (JP); Satoshi Wakai, Nasushiobara (JP); Takuya Sakaguchi, Utsunomiya (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 0 days.

(21) Appl. No.: 17/864,292

(22) Filed: Jul. 13, 2022

(65) Prior Publication Data
US 2022/0351380 A1 Nov. 3, 2022

Related U.S. Application Data

(60) Division of application No. 16/163,107, filed on Oct. 17, 2018, now Pat. No. 11,423,532, which is a (Continued)

(30) Foreign Application Priority Data

Aug. 16, 2012 (JP) ................................. 2012-180416
Aug. 31, 2012 (JP) ................................. 2012-192426

(51) Int. Cl.
*A61B 5/00* (2006.01)
*A61B 5/0205* (2006.01)
(Continued)

(52) U.S. Cl.
CPC .......... *G06T 7/0012* (2013.01); *A61B 5/0205* (2013.01); *A61B 5/0215* (2013.01);
(Continued)

(58) Field of Classification Search
CPC ....... A61B 5/0205; A61B 5/0245; A61B 6/12; A61B 6/504; A61B 6/507; A61B 6/5217; A61B 6/481; A61B 6/485
See application file for complete search history.

(56) References Cited

U.S. PATENT DOCUMENTS

2006/0241465 A1 10/2006 Huennekens
2010/0234698 A1 9/2010 Manstrom
(Continued)

FOREIGN PATENT DOCUMENTS

JP 2003-525067 8/2003
JP 2004-528920 9/2004
(Continued)

OTHER PUBLICATIONS

Japanese Office Action dated Oct. 4, 2022 in Japanese Patent Application No. 2021-162615, 3 pages.
(Continued)

*Primary Examiner* — Joel F Brutus
(74) *Attorney, Agent, or Firm* — Oblon, McClelland, Maier & Neustadt, L.L.P.

(57) ABSTRACT

According to embodiment, an image processing apparatus comprising a specifying unit and a display controller. The specifying unit that specifies an acquisition position of an indicator relating to blood flow on a blood vessel-containing image collected by a medical image diagnostic apparatus. The display controller that displays the acquisition position on the blood vessel-containing image and displays the indicator on a display unit in association with the acquisition position.

11 Claims, 29 Drawing Sheets

Related U.S. Application Data division of application No. 14/622,702, filed on Feb. 13, 2015, now Pat. No. 10,140,700, which is a continuation of application No. PCT/JP2013/072015, filed on Aug. 16, 2013.

(51) Int. Cl.
| | |
|---|---|
| *A61B 5/0215* | (2006.01) |
| *A61B 5/0245* | (2006.01) |
| *A61B 6/00* | (2006.01) |
| *A61B 6/12* | (2006.01) |
| *A61B 6/50* | (2024.01) |
| *G06T 7/00* | (2017.01) |
| *A61B 5/022* | (2006.01) |

(52) U.S. Cl.
CPC ............ *A61B 5/0245* (2013.01); *A61B 6/12* (2013.01); *A61B 6/503* (2013.01); *A61B 6/504* (2013.01); *A61B 6/507* (2013.01); *A61B 6/5217* (2013.01); *G06T 7/0016* (2013.01); *A61B 5/022* (2013.01); *A61B 6/481* (2013.01); *A61B 6/485* (2013.01); *G06T 2207/10016* (2013.01); *G06T 2207/10116* (2013.01); *G06T 2207/10121* (2013.01); *G06T 2207/20092* (2013.01); *G06T 2207/20101* (2013.01); *G06T 2207/30048* (2013.01); *G06T 2207/30104* (2013.01)

(56) References Cited

U.S. PATENT DOCUMENTS

| | | |
|---|---|---|
| 2011/0319752 A1 | 12/2011 | Steinberg et al. |
| 2012/0029339 A1* | 2/2012 | Cohen ................. A61B 8/0891 |
| | | 600/407 |
| 2012/0053918 A1 | 3/2012 | Taylor |
| 2012/0063663 A1 | 3/2012 | Kawasaki |
| 2015/0131886 A1 | 5/2015 | Aben |
| 2015/0179148 A1 | 6/2015 | Auvray |

FOREIGN PATENT DOCUMENTS

| | | |
|---|---|---|
| JP | 2010-99348 | 5/2010 |
| JP | 2010-526556 | 8/2010 |
| JP | 2011-36433 | 2/2011 |
| JP | 2011-156321 | 8/2011 |
| JP | 2012-125407 | 7/2012 |
| WO | WO 2012/021307 A2 | 2/2012 |

OTHER PUBLICATIONS

International Search Report dated Oct. 8, 2013 for PCT/JP2013/072015 (with English translation).
International Written Opinion dated Oct. 8, 2013 for PCT/JP2013/072015.
Pijls et al. (Functional measurement of coronary stenosis).

\* cited by examiner

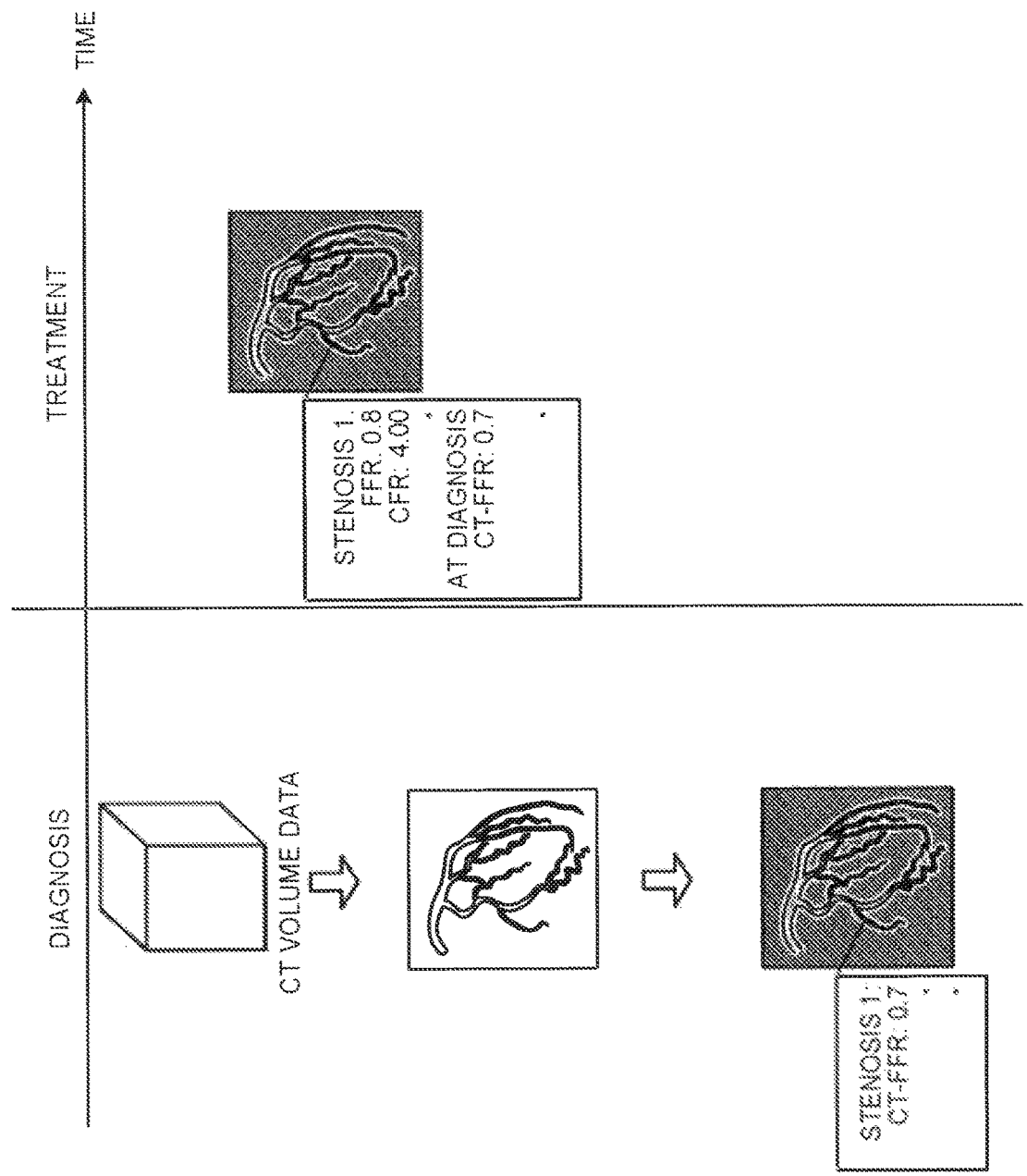

IMAGE PROCESSING APPARATUS, MEDICAL IMAGE DIAGNOSTIC APPARATUS, AND BLOOD PRESSURE MONITOR

CROSS-REFERENCE TO RELATED APPLICATIONS

This application is a divisional of U.S. application Ser. No. 16/163,107, filed on Oct. 17, 2018, which is a divisional of U.S. application Ser. No. 14/622,702, filed on Feb. 13, 2015, which is a continuation of PCT international application Ser. No. PCT/JP2013/072015 filed on Aug. 16, 2013 which designates the United States, incorporated herein by reference, and which claims the benefit of priority from Japanese Patent Application No. 2012-180416, filed on Aug. 16, 2012 and Japanese Patent Application No. 2012-192426, filed on Aug. 31, 2012, the entire contents of each of these documents are incorporated herein by reference.

FIELD

Embodiments described herein relate generally to an image processing apparatus, a medical image diagnostic apparatus, and a blood pressure monitor.

BACKGROUND

In recent years, diagnosis of coronary stenosis lesion has been made by both of "anatomical evaluation" of morphologically evaluating the presence or absence of the stenosis, the degree of the stenosis, and the like and "physiological evaluation" of objectively evaluating the presence or absence of myocardial ischemia, the degree of the myocardial ischemia, and the like. As physiological indicators to be used for the "physiological evaluation", a fractional flow reserve (FFR), a coronary flow reserve (CFR), and the like, get attention. For example, the FFR is an indicator indicating the degree of myocardial ischemia caused by the coronary stenosis. The FFR is indicated by a ratio of a maximum coronary blood flow rate under the presence of the stenosis and a maximum coronary blood flow rate under the absence of the stenosis. For example, the CFR is an indicator indicating capability to increase the coronary blood flow rate in accordance with increase in oxygen demand on the myocardium. The CFR is indicated by a ratio of a coronary blood flow rate at rest and a coronary blood flow rate at maximum reactive hyperemia.

Conventionally, these physiological indicators are calculated by a predetermined measuring device. The measuring device, for example, has a pressure sensor-equipped guide wire (pressure wire) and measures an intracoronary pressure so as to calculate the FFR. Furthermore, for example, the measuring device has a guide wire (Doppler wire) mounted with an ultrasound probe on a front end thereof and measures a blood flow velocity of the coronary artery with the ultrasound probe so as to calculate the CFR.

Conventional examples are described in Japanese Translation of PCT Application Publication No. 2010-526556, Japanese Translation of PCT Application Publication No. 2004-528920, Japanese Translation of PCT Application Publication No. 2003-525067, and Japanese Laid-open Patent Publication No. 2011-156321.

BRIEF DESCRIPTION OF THE DRAWINGS

FIG. 32 is a view illustrating generation of a display image and a display example in another embodiment.

DETAILED DESCRIPTION

According to embodiment, an image processing apparatus comprising a specifying unit and a display controller. The specifying unit that specifies an acquisition position of an indicator relating to blood flow on a blood vessel-containing image collected by a medical image diagnostic apparatus. The display controller that displays the acquisition position on the blood vessel-containing image and displays the indicator on a display unit in association with the acquisition position. Hereinafter, an image processing apparatus, a medical image diagnostic apparatus, and a blood pressure monitor according to embodiments will be described with reference to the accompanying drawings. In first to fifth embodiments, described are embodiments of an X-ray diagnostic apparatus 100.

First Embodiment

Figure 1:
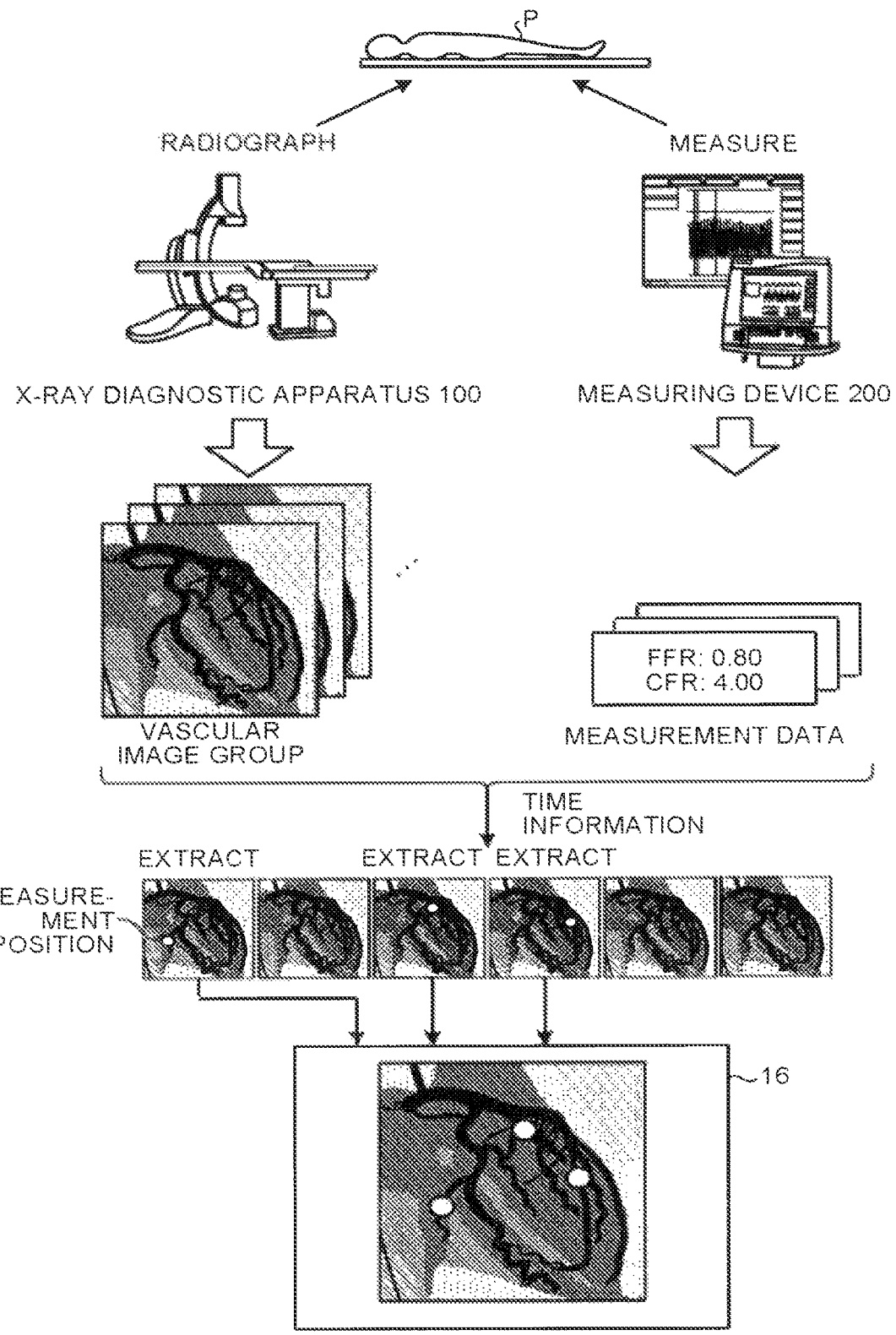
FIG. 1 is a view illustrating outline of a first embodiment.

FIG. 1 is a view illustrating outline of a first embodiment. As illustrated in FIG. 1, in the first embodiment, the X-ray diagnostic apparatus 100 collects a blood vessel-containing image of a subject P while a measuring device 200 measures an FFR, a CFR, an instantaneous wave-free ratio (iFR), an index of microcirculatory resistance (IMR), and the like. For example, an operator inserts a pressure sensor-equipped guide wire of the measuring device 200 into a coronary artery of the subject P while checking the blood vessel-containing image collected by the X-ray diagnostic apparatus 100 so as to measure an intravascular pressure. Furthermore, the operator measures intravascular pressures at a plurality of positions in the coronary artery while appropriately moving the pressure sensor-equipped guide wire. It is noted that the blood vessel-containing image (hereinafter, referred to as vascular image) indicates an image acquired with blood vessels such as the coronary artery as targets and includes an X-ray image collected under contrast imaging and an X-ray image collected under non-contrast imaging. When the X-ray diagnostic apparatus 100 collects the X-ray image under contrast imaging, for example, the blood vessel-containing image means a contrast X-ray image. When the X-ray diagnostic apparatus 100 collects the X-ray image under non-contrast imaging, the blood vessel-containing image means a non-contrast X-ray image.

As illustrated in FIG. 1, the X-ray diagnostic apparatus 100 stores, in a storage unit, a time-series vascular image group collected during the measurement of the intravascular pressures. On the other hand, the measuring device 200 calculates the FFR, the CFR, and the like based on measurement data of the intravascular pressure. The X-ray diagnostic apparatus 100 relates the time-series vascular image group collected during the measurement of the intravascular pressures to the pieces of measurement data measured by the measuring device 200.

To be specific, the time-series vascular image group collected by the X-ray diagnostic apparatus 100 includes pieces of time information at which the respective vascular images are acquired. On the other hand, the pieces of measurement data of the intravascular pressures also include pieces of time information at which the respective pieces of measurement data are measured. The X-ray diagnostic apparatus 100 relates the vascular image group to the pieces of measurement data by using the pieces of time information. The X-ray diagnostic apparatus 100 extracts a vascular image corresponding to a time phase at which each piece of measurement data is measured from the vascular image group. Then, the X-ray diagnostic apparatus 100 specifies a front end of the guide wire by image analysis of the extracted vascular image so as to specify a measurement position of each piece of measurement data. Furthermore, the X-ray diagnostic apparatus 100 displays an indicator calculated from the measurement data in association with the measurement position specified on the vascular image.

Figure 2:
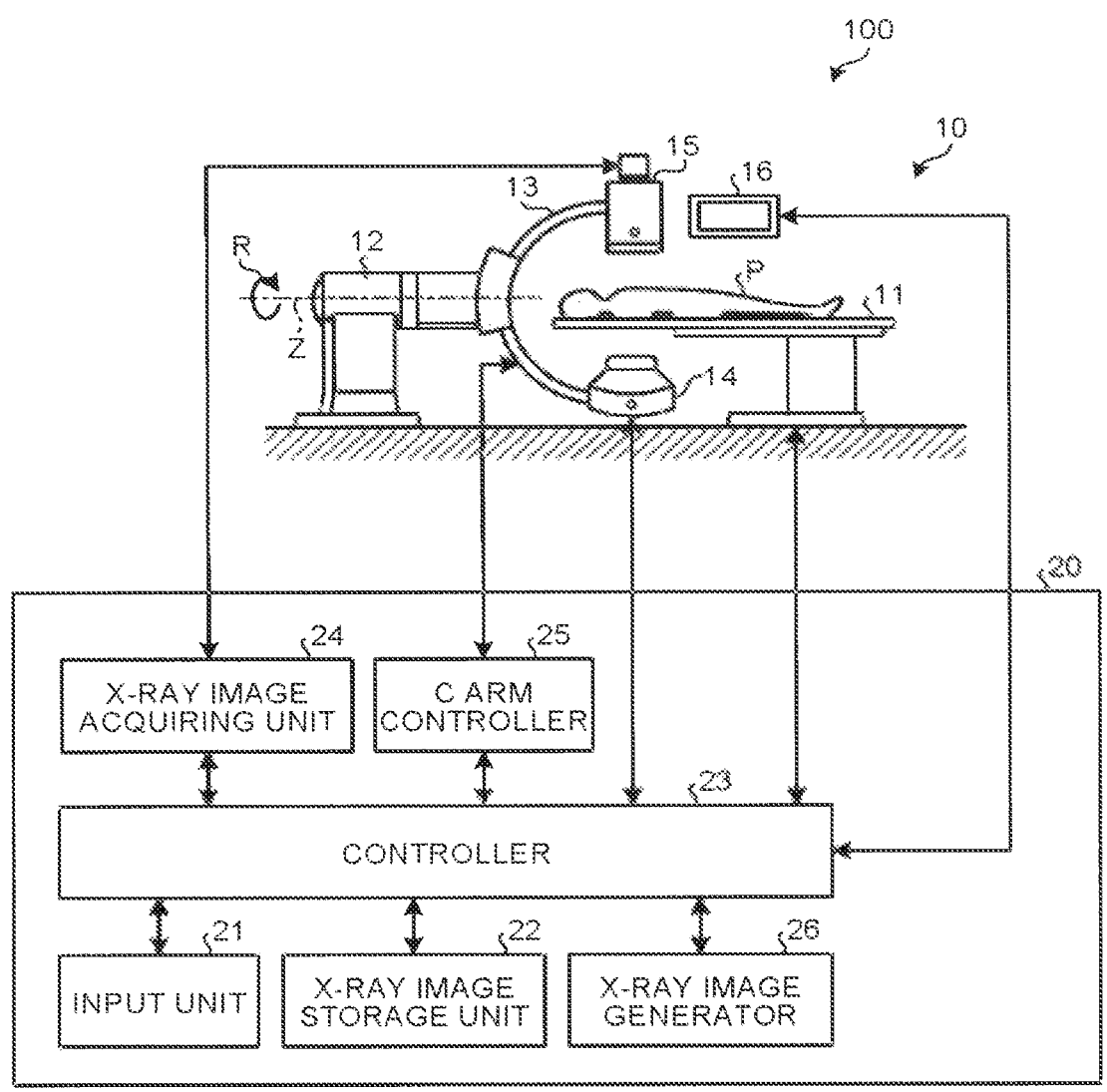
FIG. 2 is a block diagram illustrating an overall configuration of an X-ray diagnostic apparatus in the first embodiment.

FIG. 2 is a block diagram illustrating an overall configuration of the X-ray diagnostic apparatus 100 according to the first embodiment. The X-ray diagnostic apparatus 100 according to the first embodiment is a medical image diagnostic apparatus that supports endovascular therapy by using a catheter or the like while performing angiography. A function thereof for acquiring processing can be executed by using an existing known technique. As illustrated in FIG. 2, the X-ray diagnostic apparatus 100 includes a mount unit 10 and a calculator system 20. As illustrated in FIG. 2, the mount unit 10 includes a table 11, a mount 12, a C arm 13, an X-ray source 14, an X-ray detector 15, and a display unit 16.

The table 11 is movable in the perpendicular direction and the horizontal direction and the subject P is placed on the table 11. The mount 12 supports the C arm 13. The C arm 13 is rotatable in the direction of an arrow R about a Z axis and holds the X-ray source 14 and the X-ray detector 15 in an opposed manner. The X-ray source 14 includes an X-ray tube for emitting X rays and a collimator. The X-ray detector 15 detects the X rays that are emitted from the X-ray source 14 and transmit through the subject P. The display unit 16 displays an X-ray image and the like generated by the calculator system 20.

The calculator system 20 includes an input unit 21, an X-ray image storage unit 22, a controller 23, an X-ray image acquiring unit 24, a C arm controller 25, and an X-ray image generator 26.

The input unit 21 is a control panel, a foot switch, or the like, and receives inputs of various types of operations onto the X-ray diagnostic apparatus 100 from an operator. The X-ray image storage unit 22 stores therein X-ray image data. The controller 23 controls the X-ray diagnostic apparatus 100 overall. The X-ray image acquiring unit 24 controls the X-ray source 14, the X-ray detector 15, and the C arm controller 25 and acquires an X-ray image. Furthermore, the X-ray image acquiring unit 24 transmits the acquired X-ray image to the X-ray image generator 26. The C arm controller 25 controls rotation and the like of the C arm 13 under control of the X-ray image acquiring unit 24. The X-ray image generator 26 generates the X-ray image.

Figure 3:
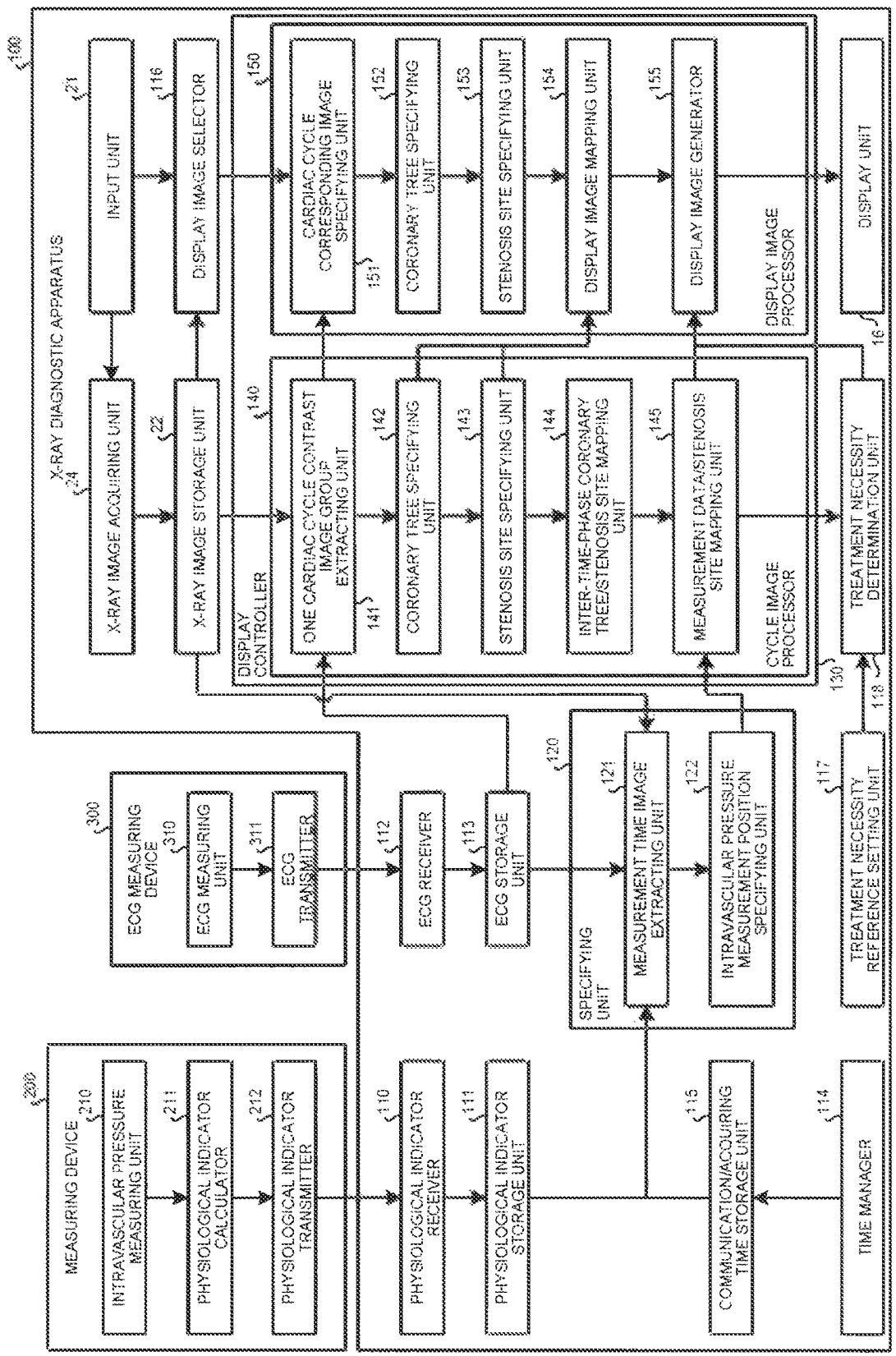
FIG. 3 is a diagram illustrating configurations of the X-ray diagnostic apparatus, a measuring device, and an electrocardiogram (ECG) measuring device in the first embodiment.

FIG. 3 is a diagram illustrating configurations of the X-ray diagnostic apparatus 100, the measuring device 200, and an ECG measuring device 300 according to the first embodiment. FIG. 3 illustrates a partial configuration (configuration in which measurement data and the X-ray image are analyzed and the image and a character string are displayed) of the X-ray diagnostic apparatus 100 as illustrated in FIG. 2 in detail. In FIG. 3, the same reference numerals as those in FIG. 2 denote the same parts and description thereof is omitted. Furthermore, it is sufficient that the respective parts other than the display unit 16, the input unit 21, the X-ray image storage unit 22, and the X-ray image acquiring unit 24 among the parts included in the X-ray diagnostic apparatus 100 in FIG. 3 are included in the controller 23 or the like as illustrated in FIG. 2.

The measuring device 200 and the ECG measuring device 300 are capable of being achieved by using existing known techniques. First, the measuring device 200 measures an intravascular pressure and the like, calculates the FFR and the CFR based on measurement data obtained by the measurement, and transmits the calculated FFR and CFR to the X-ray diagnostic apparatus 100 for each measurement. To be specific, an intravascular pressure measuring unit 210 measures an intravascular pressure and the like and transmits measurement data to a physiological indicator calculator 211. The physiological indicator calculator 211 calculates the FFR and the CFR based on the measurement data and transmits the calculated FFR and CFR to a physiological indicator transmitter 212. The physiological indicator transmitter 212 transmits the FFR and the CFR to the X-ray diagnostic apparatus 100. The physiological indicator transmitter 212 may transmit the measurement data itself measured by the intravascular pressure measuring unit 210 in addition to the FFR and the CFR to the X-ray diagnostic apparatus 100.

Furthermore, the ECG measuring device 300 measures an ECG and transmits the measured ECG to the X-ray diagnostic apparatus 100 for each measurement. To be specific, an ECG measuring unit 310 measures an ECG and transmits the measured ECG to an ECG transmitter 311. The ECG transmitter 311 transmits the ECG to the X-ray diagnostic apparatus 100.

The X-ray diagnostic apparatus 100 relates a time-series X-ray image group acquired during measurement of the pieces of measurement data to the pieces of measurement data, specifies a measurement position of each piece of measurement data on X-ray image, and displays the X-ray image indicating the measurement position on the display unit 16.

To be more specific, a physiological indicator receiver 110 receives the FFR and the CFR from the measuring device 200 and stores them in a physiological indicator storage unit 111. Furthermore, an ECG receiver 112 receives the ECG from the ECG measuring device 300 and stores it in an ECG storage unit 113. A time manager 114 manages the right time in the X-ray diagnostic apparatus 100. Each time the X-ray diagnostic apparatus 100 communicates with the measuring device 200 or the ECG measuring device 300 or each time the X-ray image acquiring unit 24 acquires an X-ray image, the time manager 114 stores a communication time or an acquiring time in a communication/acquiring time storage unit 115.

In the first embodiment, it is supposed that the X-ray diagnostic apparatus 100, the measuring device 200, and the ECG measuring device 300 are in a state where the time is set to be right. The X-ray diagnostic apparatus 100 makes temporal synchronization between various pieces of information received from the measuring device 200 and the ECG measuring device 300 and the X-ray image acquired by the X-ray diagnostic apparatus 100 in accordance with the time managed by the time manager 114. It is needless to say that the embodiment is not limited thereto. The X-ray diagnostic apparatus 100, for example, may make temporal synchronization by transmitting a temporal synchronization signal to the measuring device 200 and the ECG measuring device 300.

Figure 4:
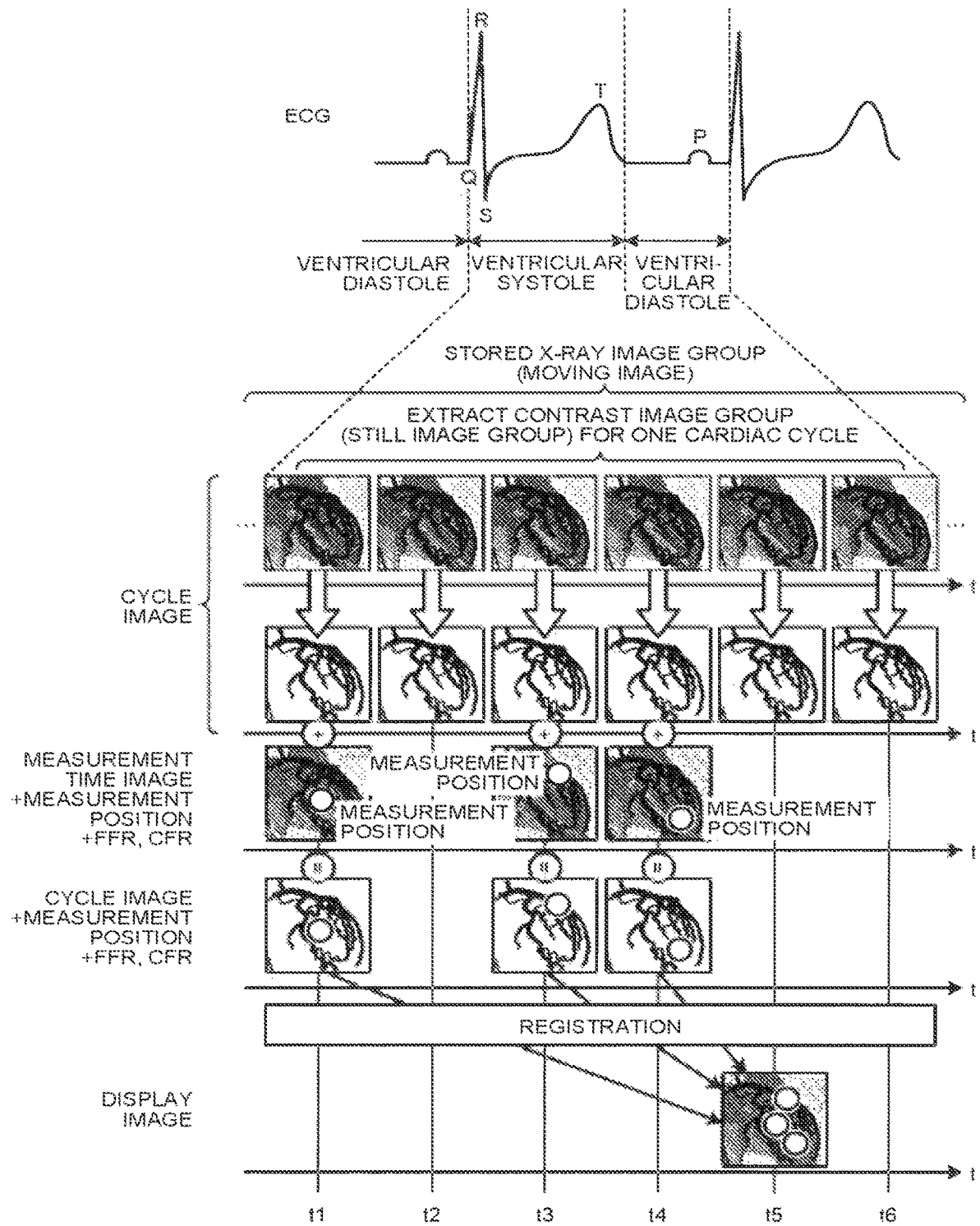
FIG. 4 is a view for explaining generation of a display image in the first embodiment.

Subsequently, described are a specifying unit 120 and a display controller 130 with reference to FIG. 4. FIG. 4 is a view for explaining generation of a display image in the first embodiment.

The specifying unit 120 specifies an acquisition position of an indicator relating to blood flow on a blood vessel-containing image collected by the medical image diagnostic apparatus. To be specific, the specifying unit 120 specifies a measurement position of measurement data on an X-ray image collected by the X-ray diagnostic apparatus 100. To be more specific, a measurement time image extracting unit 121 extracts an X-ray image (measurement time image) corresponding to a time phase at which the measurement data is measured from the time-series X-ray image group that is acquired by the X-ray image acquiring unit 24 and stored in the X-ray image storage unit 22. The measurement time image extracting unit 121, for example, uses time information corresponding to the FFR and the CFR that is received from the measuring device 200, time information corresponding to the ECG that is received from the ECG measuring device 300, and time information corresponding to the X-ray image so as to relate these pieces of information collected at a given time to one another. This makes it possible to make temporal synchronization among the pieces of information collected by different devices. The measurement time image extracting unit 121 extracts an X-ray image having the time information that is substantially the same as the time information corresponding to the FFR and the CFR, as the X-ray image corresponding to the time phase at which the measurement data is measured. Then, the measurement time image extracting unit 121 transmits the extracted X-ray image to an intravascular pressure measurement position specifying unit 122.

The intravascular pressure measurement position specifying unit 122 specifies a measurement position of the measurement data on the X-ray image (measurement time image) extracted by the measurement time image extracting unit 121. The intravascular pressure measurement position specifying unit 122, for example, performs image analysis on the X-ray image extracted by the measurement time image extracting unit 121 and specifies the front end of the guide wire used for the measurement so as to specify the measurement position.

The front end of the guide wire is capable of being specified by an existing known technique. The intravascular pressure measurement position specifying unit 122, for example, performs emphasis processing on the X-ray image so as to clarify an image of the guide wire. The intravascular pressure measurement position specifying unit 122, for example, performs non-linear brightness conversion so as to reduce unevenness in the density of the X-ray image, and then performs image filtering processing of extracting a component having a high spatial frequency. The image filtering processing removes global smooth gradation and makes only local fine fluctuating components left. Next, the intravascular pressure measurement position specifying unit 122 performs pattern extraction processing on the X-ray image so as to specify the image of the guide wire. The intravascular pressure measurement position specifying unit 122, for example, performs pixel value threshold processing, spatial filtering processing, or the like. Then, the intravascular pressure measurement position specifying unit 122 extracts the image of the guide wire from the X-ray image, obtains a two-dimensional curve indicating a shape of the image of the guide wire on the X-ray image, and extracts coordinates of the front end of the guide wire located at an end portion of the two-dimensional curve based on coordinate values of respective points on the two-dimensional curve.

The display controller 130 displays an acquisition position on the blood vessel-containing image and displays the indicator on the display unit in association with the acquisition position. The display controller 130, for example, displays the measurement position on the X-ray image and displays the FFR and the CFR thereon in association with the measurement position. First, a one cardiac cycle contrast image group extracting unit 141 of a cycle image processor 140 extracts a contrast image group (still image group) for one cardiac cycle on which the coronary artery overall is contrast-imaged preferably from the time-series X-ray image group stored in the X-ray image storage unit 22, as illustrated in FIG. 4. It is noted that the one cardiac cycle contrast image group extracting unit 141, for example, compares brightness value distributions of the respective X-ray images and determines an X-ray image group having low brightness value to be the contrast image group on which the coronary artery is contrast-imaged preferably.

As illustrated in FIG. 4, a coronary tree specifying unit 142 extracts a coronary artery region from each contrast image of the contrast image group extracted by the one cardiac cycle contrast image group extracting unit 141 so as to specify a coronary tree. The coronary tree specifying unit 142, for example, extracts the coronary artery region from each contrast image based on acquiring conditions such as the angle of the C arm 13, brightness values of pixels, continuity thereof, a vascular shape, and a change amount between the contrast images at adjacent time phases so as to specify the coronary tree. It is noted that the coronary tree is capable of being specified by an existing known technique.

A stenosis site specifying unit 143 specifies a stenosis site in the coronary artery region extracted by the coronary tree specifying unit 142. The stenosis site specifying unit 143, for example, specifies the stenosis site based on continuity of a vascular structure, in particular, change in the vascular diameter. It is noted that the stenosis site is capable of being specified by an existing known technique.

An inter-time-phase coronary tree/stenosis site mapping unit 144 relates the stenosis sites specified on the respective contrast images of the contrast image group for one cardiac cycle among different time phases. This makes it possible to track the time-series displacement of the stenosis site on the X-ray images. The inter-time-phase coronary tree/stenosis site mapping unit 144, for example, calculates a WarpField among the contrast images. The WarpField is a known image processing technique of performing non-linear positioning. The inter-time-phase coronary tree/stenosis site mapping unit 144, for example, extracts characteristic amounts from the respective contrast images and relates the extract characteristics among the different time phases so as to calculate a set of three-dimensional vectors indicating movement amounts of pixels.

As illustrated in FIG. 4, a measurement data/stenosis site mapping unit 145 relates the measurement data to the stenosis site specified on the contrast image (cycle image) based on the measurement position specified on the X-ray image (measurement time image) by the intravascular pressure measurement position specifying unit 122. The measurement data/stenosis site mapping unit 145, for example, specifies a contrast image (cycle image) of which time phase is identical to that of the measurement time image in the contrast image group for one cardiac cycle by using the ECG. Then, the measurement data/stenosis site mapping unit 145 relates the FFR and the CFR that are calculated from the measurement data measured at the measurement position to and the stenosis site on the contrast image (cycle image) that is closer to the measurement position based on the measurement position specified on the X-ray image (measurement time image). This makes it possible to display the FFR and the CFR on each of the X-ray images contained in the time-series X-ray image group.

On the other hand, a cardiac cycle corresponding image specifying unit 151 of a display image processor 150 specifies a time phase on one cardiac cycle to which a display image selected by a display image selector 116 corresponds by using the ECG. It is sufficient that the display image selector 116 receives a direction from the operator through the input unit 21 so as to appropriately select a display image from the time-series X-ray image group stored in the X-ray image storage unit 22, for example. In the first embodiment, the display image selector 116, for example, displays a selection menu (for example, "patient list" and "test list") of the X-ray images stored in the X-ray image storage unit 22, receives a direction from the operator through the input unit 21, and selects a single contrast image (still image) as the display image.

A coronary tree specifying unit 152 extracts a coronary artery region from the contrast image at the time phase specified by the cardiac cycle corresponding image specifying unit 151 in the contrast image group extracted by the one cardiac cycle contrast image group extracting unit 141 with the same method as that by the coronary tree specifying unit 142 so as to specify a coronary tree. A stenosis site specifying unit 153 specifies a stenosis site in the coronary artery region extracted by the coronary tree specifying unit 152 with the same method as that by the stenosis site specifying unit 143.

As illustrated in FIG. 4, a display image mapping unit 154 relates the measurement position specified on the contrast image (cycle image) to the display image. The display image mapping unit 154, for example, specifies (positions) a position at a time phase of the display image to which the measurement position specified on the contrast image (cycle image) is moved with a three-dimensional vector by using the WarpField calculated by the inter-time-phase coronary tree/stenosis site mapping unit 144. Then, the display image mapping unit 154 specifies a plurality of measurement positions specified on the contrast images at different time phases on one display image. That is to say, the display image mapping unit 154 specifies positions at the time phase of the display image to which the respective measurement positions are moved by using the WarpField. This corrects deviation between a single contrast image selected as the display image and the respective contrast images on which the respective measurement positions are specified.

Figure 5:
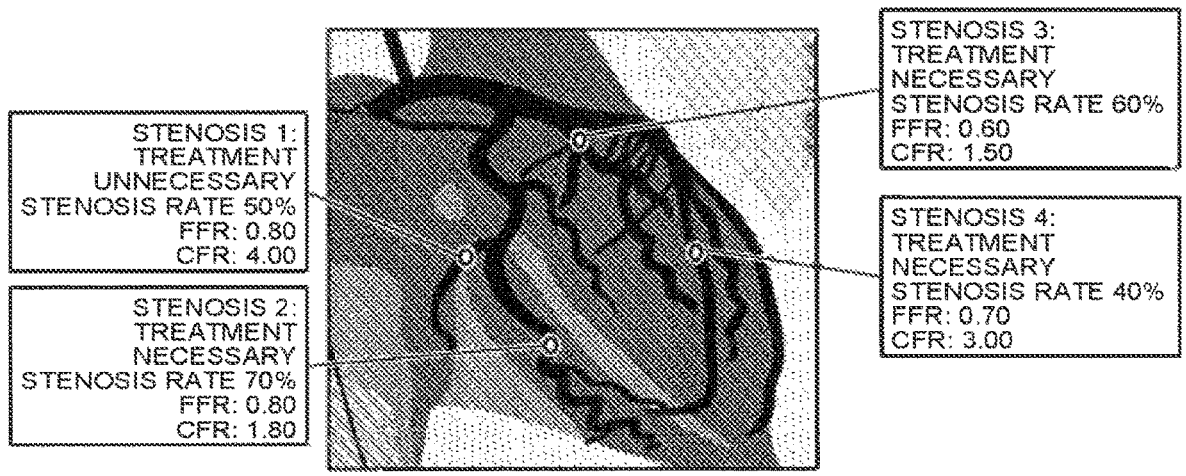
FIG. 5 is a view illustrating a display example in the first embodiment.

A display image generator 155 generates the display image and displays it on the display unit 16. FIG. 5 is a view illustrating a display example in the first embodiment. As illustrated in FIG. 5, in the first embodiment, the display image generator 155 displays the measurement positions of the pieces of measurement data on an X-ray image (still image) at a predetermined time phase. In addition, the display image generator 155 displays the physiological evaluation indicators (for example, FFR and CFR) calculated from the pieces of measurement data in association with the measurement positions. Furthermore, the display image generator 155 displays a stenosis rate in association with each stenosis site so as to display an anatomical evaluation indicator and the physiological evaluation indicators on the same X-ray image. As illustrated in FIG. 5, the display image generator 155 displays information (for example, treatment unnecessary and treatment necessary) relating to necessity of treatment. Marks (in FIG. 5, outlined circles) indicating the stenosis sites may be displayed in different colors in accordance with the necessity of treatment, the stenosis rate, and the like, for example. Furthermore, character strings and frames surrounding the character strings may be displayed in different colors in accordance with the necessity of treatment and values of the FFR and the CFR, for example. For example, they may be displayed in "red" when an attention should be paid.

A treatment necessity reference setting unit 117 sets a reference for determining necessity of treatment. The treatment necessity reference setting unit 117, for example, sets a reference that "when any of conditions: FFR<0.75; CFR≤2.00; and stenosis rate 50% is satisfied, it is determined to be "treatment necessary"". A treatment necessity determination unit 118 determines the necessity of treatment based on the reference set by the treatment necessity reference setting unit 117. It is noted that a determination result by the treatment necessity determination unit 118 is transmitted to the display image generator 155.

Figure 6:
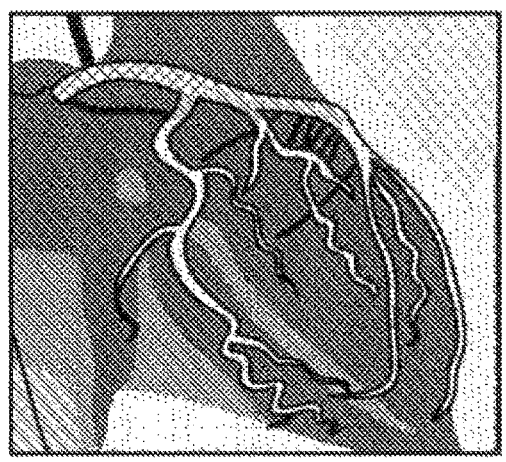
FIG. 6 is a view illustrating another display example in the first embodiment.

FIG. 6 is a view illustrating another display example in the first embodiment. As illustrated in FIG. 6, in the first embodiment, the display image generator 155 may not only display various types of indicators (display of the various types of indicators are not illustrated in FIG. 6) around the stenosis sites but also display the blood vessels themselves while varying the colors and the densities in accordance with the measurement values of the intravascular pressure and the like. In FIG. 6, the blood vessels themselves are displayed while varying the color density for the convenience. Alternatively, the blood vessels may be displayed while varying densities of "red" and "yellow" or the like in accordance with the measurement values, for example.

Figure 7:
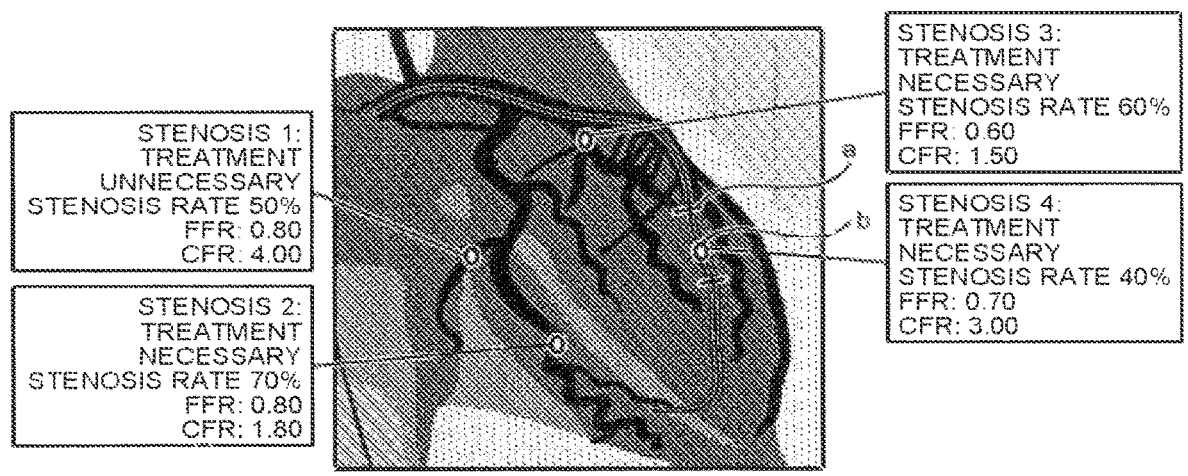
FIG. 7 is a view illustrating still another display example in the first embodiment.

FIG. 7 is a view illustrating still another display example in the first embodiment. As illustrated in FIG. 7, in the first embodiment, the display image generator 155 may display a tool for adjusting a result of automatic processing manually. That is to say, as described above, although the stenosis sites, the measurement positions of the pieces of measurement data, and the like are specified on the X-ray image automatically to be displayed in the first embodiment, there is a risk that an expected result is not necessarily displayed. For the purpose of coping with the case, the display image generator 155 displays a user interface (UI) as illustrated in FIG. 7. The UI, for example, extracts a vascular core line from the coronary tree specified by the coronary tree specifying unit 142 and displays the extracted vascular core line. The display image generator 155 receives slide operations of a bar "a" indicating the measurement position and a mark "b" indicating the stenosis site on the vascular core line. That is to say, the measurement positions and the stenosis sites should be present on the vascular core line (deviation from the core line in the vascular diameter is neglected), so that the display image generator 155 may provide a UI slidable on the vascular core line only.

As described above, according to the first embodiment, the measurement positions of the pieces of measurement data are displayed on the vascular image, so that the measurement positions of the physiological indicators can be grasped on the vascular image. Thus, according to the first embodiment, a result of the physiological evaluation and a result of the anatomical evaluation are related to be displayed. As a result, the operator is capable of grasping the position of the coronary artery at which the physiological evaluation indicators are obtained easily, for example. It is effective not only in the case of normal lesion but also in the cases of continuous lesion and multivessel lesion.

In this manner, according to the first embodiment, physiological evaluation indicators linked with a stenosis position on an X-ray image that is acquired in real time during percutaneous coronary intervention (PCI) and past images stored in a workstation or the like can be displayed. Furthermore, an intravascular pressure and a value of the blood flow velocity that are measured for calculating the physiological evaluation indicators can be also displayed at the measured position. As a result, inducibility of myocardial ischemia by the coronary artery stenosis can be evaluated from both of anatomical and physiological perspectives on a single image, and a procedure can be performed while displaying the necessity of treatment and a treatment state during the PCI. Furthermore, when physiological evaluation values are displayed on a past test image, the past state can be compared with the present state quantitatively physiologically.

Second Embodiment

Figure 8:
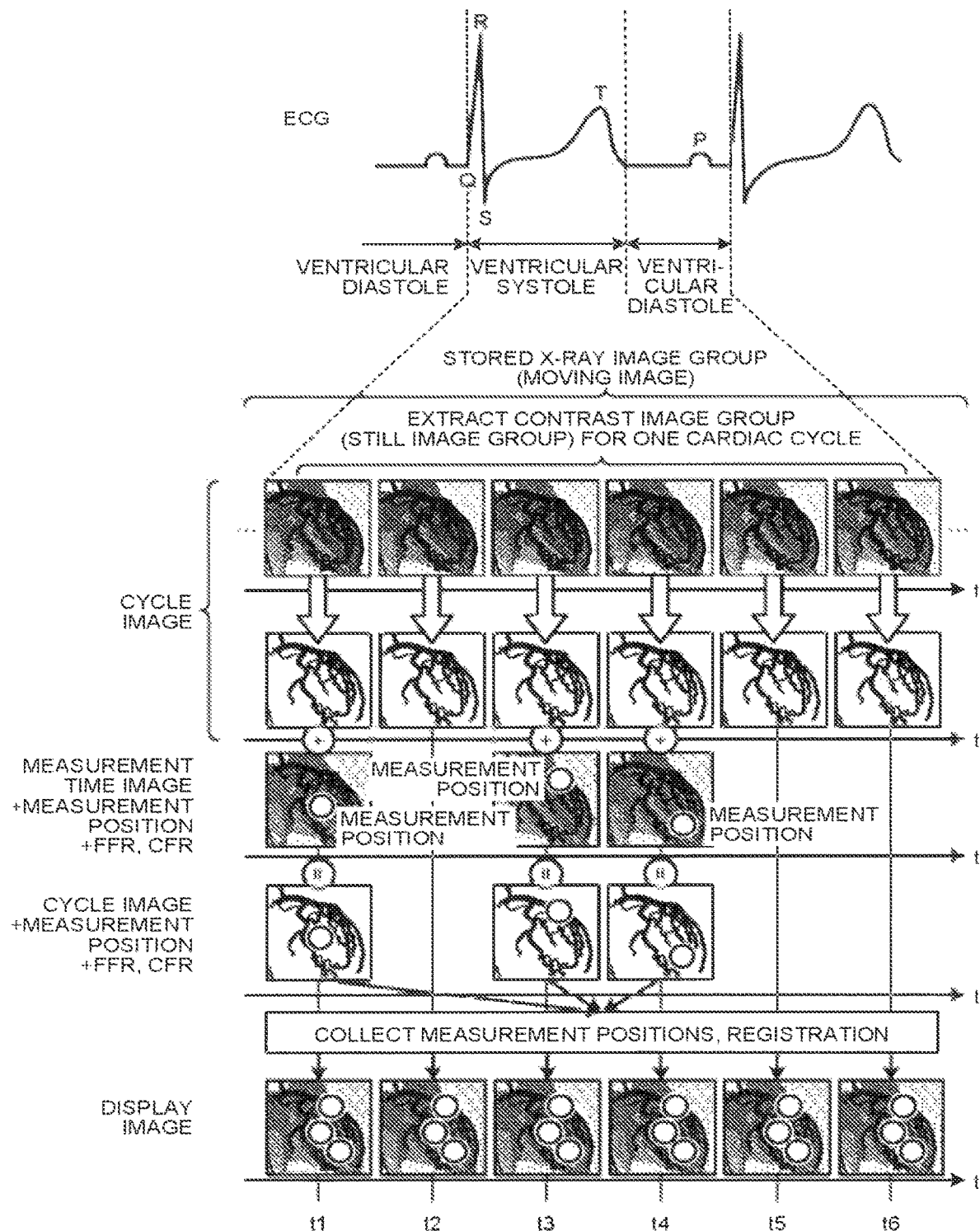
FIG. 8 is a view for explaining generation of display images in a second embodiment.

In a second embodiment, a time-series X-ray image group (moving image) acquired in real time is supposed as display images. FIG. 8 is a view for explaining generation of the display images in the second embodiment. In this case, the display controller 130 makes temporal synchronization between the contrast image (cycle image) group and the display image group by using the ECG and displays stenosis sites specified on the contrast images (cycle images) and indicators such as the FFR and the CFR on right positions on the display images.

To be specific, the cardiac cycle corresponding image specifying unit 151 of the display image processor 150 specifies time phases in one cardiac cycle to which respective display images contained in the time-series display image groups correspond by using the ECG. Furthermore, as illustrated in FIG. 8, the display image mapping unit 154 relates the measurement positions specified on the contrast images (cycle images) to the respective display images contained in the time-series display image groups. The display image mapping unit 154, for example, specifies (positions) positions at time phases of the respective display images to which the measurement positions specified on the contrast images (cycle images) are moved with three-dimensional vectors by using the WarpField calculated by the inter-time-phase coronary tree/stenosis site mapping unit 144. Then, the display image mapping unit 154 specifies a plurality of measurement positions specified on the contrast images at different time phases on the respective display images. When the display images are displayed sequentially while measuring the pieces of measurement data, it is sufficient that the display controller 130 displays one measurement position on the display images first, and displays two measurement positions, and three measurement positions thereon sequentially.

Third Embodiment

Figure 9:
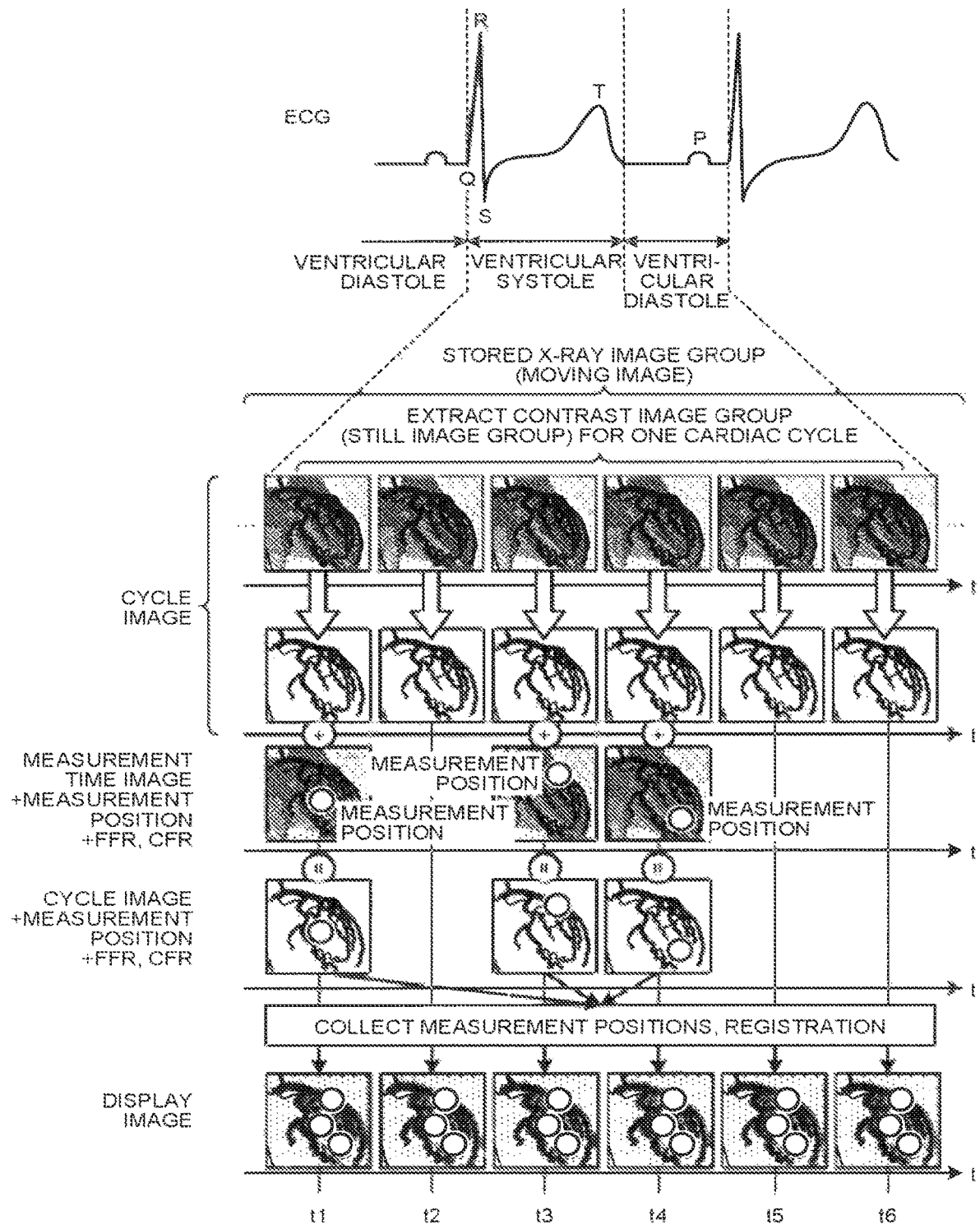
FIG. 9 is a view for explaining generation of display images in a third embodiment.

In a third embodiment, a time-series X-ray image group (moving image) acquired in real time that is non-contrast images is supposed as display images. FIG. 9 is a view for explaining generation of the display images in the third embodiment. In this case, the display images are the non-contrast images, so that the vascular structure of the coronary artery is not displayed on the display images. The display controller 130 extracts pieces of structural information such as vascular contours from the contrast image (cycle image) group and displays the extracted pieces of structural information so as to be superimposed on the display image group that is the non-contrast images. The display controller 130 makes temporal synchronization between the contrast image (cycle image) group and the display image group by using the ECG so as to also make temporal synchronization between the structural information and the display images. With this, displacement and deformation of blood vessels are also reflected onto the structural information.

Figure 10:
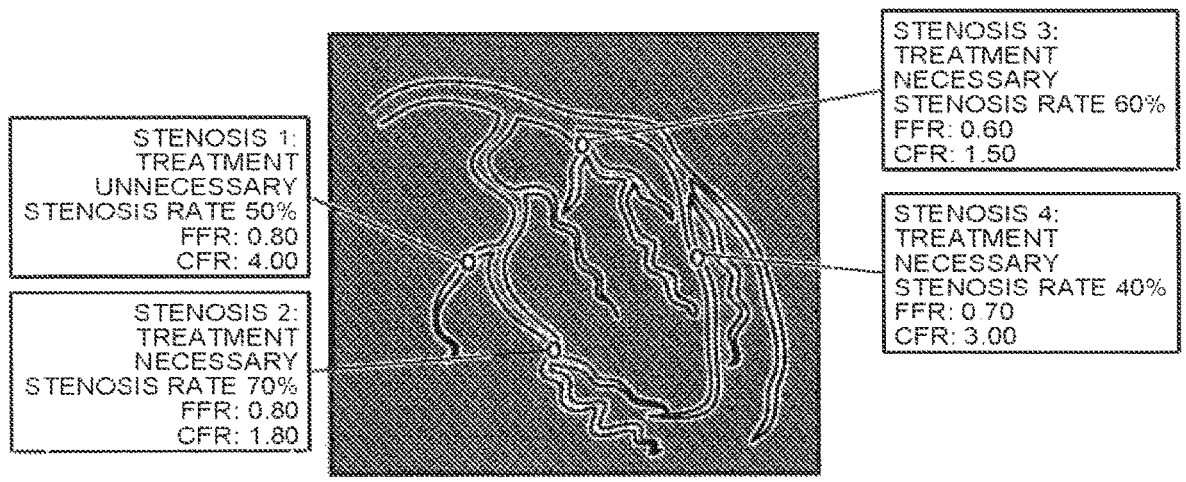
FIG. 10 is a view illustrating a display example in the third embodiment.

FIG. 10 is a view illustrating a display example in the third embodiment. As illustrated in FIG. 10, in the third embodiment, the display controller 130 displays physiological evaluation indicators, stenosis rates, necessity of treatment, and the like on each non-contrast display image on which the structural information such as the vascular contour is displayed in the superimposed manner in association with the measurement positions of the pieces of measurement data.

Figure 11:
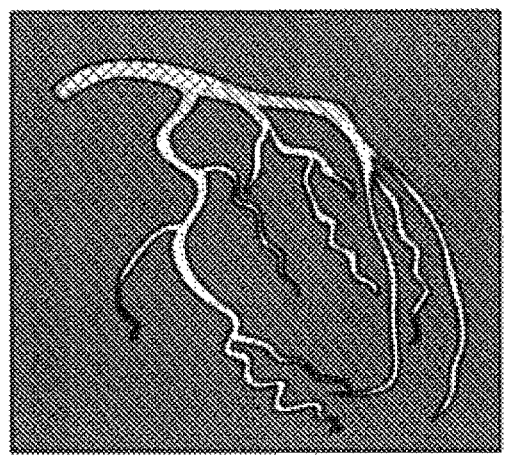
FIG. 11 is a view illustrating another display example in the third embodiment.

FIG. 11 is a view illustrating another display example in the third embodiment. As illustrated in FIG. 11, in the third embodiment, the display controller 130 may not only display various types of indicators (display of the various types of indicators are not illustrated in FIG. 11) around the stenosis sites but also display the blood vessels themselves while varying the colors and the densities in real time in accordance with the measurement values of the intravascular pressure and the like on each non-contrast display image.

Described is one use case of the X-ray diagnostic apparatus 100 serving as the medical image diagnostic apparatus according to the present application. As described above, various indicators are used as indicators relating to the blood flow. These indicators are used for detecting a vascular stenosis portion on a myocardial site that is cause of myocardial infarction early, for example. As an example, the presence or absence of the vascular stenosis portion is determined based on evaluation of lowering of the blood flow rate due to the stenosis site. When the value of the FFR (hereinafter, referred to as FFR value) is equal to or lower than the reference value, the position is determined to be a stenosis portion.

Conventionally, the presence or absence of the vascular stenosis portion has been determined as follows. That is, an operator operates a pressure sensor-equipped guide wire while checking a display displaying in real time an X-ray image (for example, X-ray fluoroscopic image) relating to a subject into whose blood vessel that is collected by the X-ray diagnostic apparatus the guide wire is inserted, and concurrently checks a display displaying an FFR value calculated from a pressure value of the subject that is measured by the pressure sensor. In this case, the FFR value and a vascular portion on which pressure that is used for calculation of the FFR value is measured are not related to each other. For this reason, even when the operator determines that the measured position is the stenosis portion based on the FFR value, it is difficult to grasp the position of the stenosis portion on the blood vessel instinctively.

For the purpose of solving this, the technique according to the present application is applied to the case so as to improve spatial visibility of an indicator effective for diagnosis of vascular stenosis. Hereinafter, described is the X-ray diagnostic apparatus 100 according to the use case with reference to FIG. 12 to FIG. 26. Note that the indicator effective for the diagnosis of the vascular stenosis is an indicator indicating the blood flow rate. Description herein is made by using the FFR value as a specific example of the indicator.

The FFR value is given as a ratio of a pressure at a given point in a blood vessel that is a diagnosis target relative to a pressure (pressure of blood flow) at a point in an aorta. The pressure is measured by a pressure sensor 210a attached to the vicinity of the front end of the guide wire. In the use case, the guide wire is inserted into the blood vessel while checking a non-contrast fluoroscopic image. The fluoroscopic image is collected repeatedly at a constant cycle such as $1/30$ sec while X rays are emitted intermittently under fluoroscopic X-ray conditions (relatively low dose). An X-ray image that is triggered by the operator to be acquired with pulse X rays under acquiring X-ray conditions (relatively high dose) under the fluoroscopic control is referred to as an acquisition image. The acquisition image that is collected while emphasizing blood vessels with a contrast material is the contrast image as described above. For example, the contrast image includes a digital angiography image (DA image) and a digital subtraction angiography (DSA) image obtained by taking a difference between DA images before and after injection of the contrast material and clarifying the blood vessels further.

Figure 12:
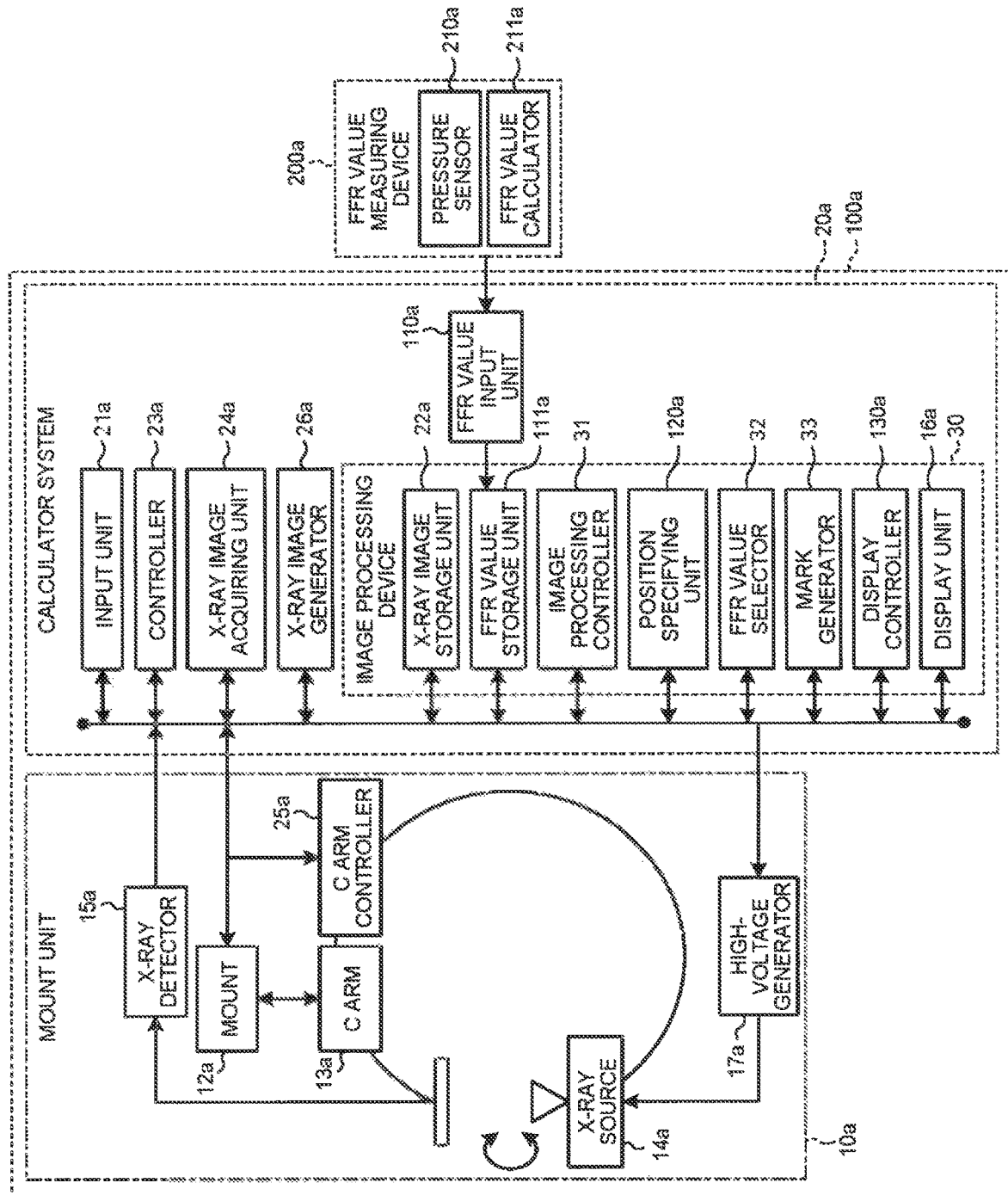
FIG. 12 is a diagram illustrating a configuration of an X-ray diagnostic apparatus according to the embodiment.
Figure 13:
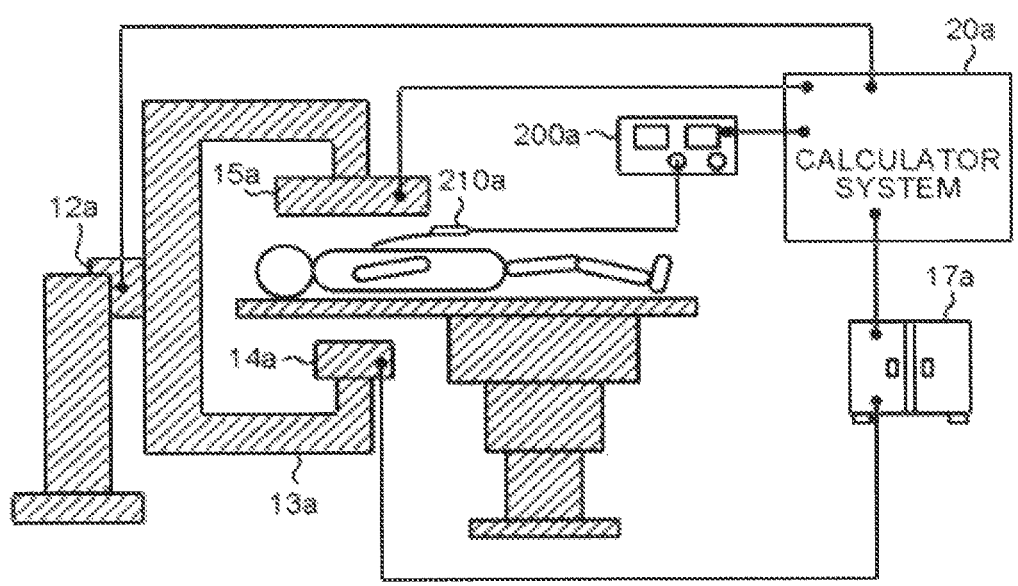
FIG. 13 is a view illustrating an outer appearance of a gantry portion in FIG. 12.

As illustrated in FIG. 12, an X-ray diagnostic apparatus 100a includes a mount unit 10a and a calculator system 20a. As illustrated in FIG. 13, the mount unit 10a includes a C arm 13a that is supported by a mount 12a. In addition, the mount unit 10a includes a C arm controller 25a, an X-ray source 14a, an X-ray detector 15a, and a high-voltage generator 17a. The mount unit 10a is also referred to as a gantry portion. The calculator system 20a is also referred to as a system main body. Furthermore, the mount 12a is also referred to as a C-shaped arm supporting mechanism. The C arm 13a is also referred to as a C-shaped arm. The C arm controller 25a is also referred to as a rotation driving unit. The X-ray source 14a is also referred to as an X-ray tube device. The X-ray detector 15a is also referred to as an X-ray detecting unit.

The calculator system 20a includes an input unit 21a, a controller 23a, an X-ray image acquiring unit 24a, an X-ray image generator 26a, and an image processing apparatus 30. The input unit 21a is also referred to as an operation unit. The controller 23a is also referred to as a system controller. The X-ray image acquiring unit 24a is also referred to as an acquiring controller. The X-ray image generator 26a is also referred to as an image generator. The image processing apparatus 30 includes an X-ray image storage unit 22a, an FFR value storage unit 111a, an FFR value input unit 110a, an image processing controller 31, a position specifying unit 120a, an FFR value selector 32, a mark generator 33, a display controller 130a, and a display unit 16a. Furthermore, an external FFR value measuring device 200a is connected to the calculator system 20a through the FFR value input unit 110a.

The FFR value storage unit 111a is an example of the above-mentioned physiological indicator storage unit 111. The FFR value input unit 110a is an example of the above-mentioned physiological indicator receiver 110. The position specifying unit 120a is an example of the above-mentioned specifying unit 120.

The controller 23a controls operations of the apparatus overall, for example, an acquiring operation and an image processing operation collectively. The X-ray image acquiring unit 24a controls the high-voltage generator 17a, the X-ray detector 15a, the X-ray image generator 26a, and the C arm controller 25a in order to execute an acquiring operation in accordance with a direction from an operator that is input through the input unit 21a.

The input unit 21a functions as a man-machine interface when the operator inputs a direction to the X-ray diagnostic apparatus 100a. For example, the input unit 21a includes a track ball, various types of switches, buttons, a mouse, a keyboard, a foot pedal, a touch panel, and the like in order to load various types of directions, conditions, a setting direction of a region of interest (ROI), various image quality conditions, an acquiring (fluoroscopic) condition setting direction, and the like from the operator on the apparatus main body. Furthermore, the input unit 21a may include a wireless receiver and a wireless processor in order to enable the operator to operate from remote places.

The mount 12a supports the C arm 13a in a rotatable manner so as to be independent with respect to perpendicular three axes. The C arm controller 25a generates a driving force for rotating the C arm 13a based on the control of the X-ray image acquiring unit 24a. The C arm 13a is mounted with the X-ray source 14a on one end thereof. The X-ray source 14a is constituted by an X-ray tube and an X-ray diaphragm. The X-ray tube generates X rays when receiving application of a high voltage from the high-voltage generator 17a. The X-ray diaphragm is attached to an X-ray emission window of the X-ray tube and limits an X-ray emission field. The C arm 13a is mounted with the X-ray detector 15a on the other end thereof. The X-ray detector 15a is attached so as to be opposed to the X-ray source 14a. The X-ray detector 15a is a two-dimensional detector for detecting X rays that transmit through the subject. The X-ray detector 15a is a flat panel detector (FPD) or the like typically.

The X-ray image generator 26a generates two-dimensional spatial distribution relating to intensity of transmitted X rays, that is, a two dimensional X-ray image based on the output from the X-ray detector 15a. The image processing controller 31 receives a control signal from the controller 23a and controls constituent components relating to the image processing operation of the X-ray diagnostic apparatus 100a, in particular. The X-ray image storage unit 22a stores therein the X-ray image generated by the X-ray image generator 26a. The X-ray image generator 26a, for example, stores therein fluoroscopic image data and contrast image (for example, DA image) data. Hereinafter, description is made by using the DA image as an example of the contrast image. Each of the fluoroscopic image data and the DA image data is stored in association with an X-ray generation time code corresponding to the data and a cardiac phase code at the time of generation of the X rays. Then, the operator selects, as a reference image, a specific DA image from a plurality of DA images stored in the X-ray image storage unit 22a.

The position specifying unit 120a selects, as a processing target, a live image at a cardiac phase same as a cardiac phase (reference phase) of the subject at the time of acquiring of the reference image, and specifies a sensor position on the reference image (DA image) from a sensor position on the selected live image. A front end region of the guide wire at the present time is expressed on the live image with a characteristic brightness. First, the position specifying unit 120a extracts the front end region of the guide wire on the live image by the threshold processing. Then, the position specifying unit 120a specifies a front end position of the guide wire based on the shape characteristic and the movement direction of the extracted front end region. Furthermore, the position specifying unit 120a shifts the position to the rear side from the front end position of the guide wire by a distance unique to the guide wire, that is, a distance L (see, FIG. 26) from the front end position of the guide wire to an attachment position of the pressure sensor 210a of the guide wire so as to specify the sensor position on the live image.

Next, the position specifying unit 120a specifies the sensor position on the reference image that corresponds to the sensor position on the live image of the present frame. First, the position specifying unit 120a calculates the direction and the distance of the sensor position specified on the live image of the present frame with respect to a sensor position specified on a live image of the last frame. Then, the position specifying unit 120a displaces the last sensor position on the reference image in the calculated direction by the calculated distance by using the calculated direction and distance. With this, the position specifying unit 120a specifies the sensor position on the reference image that corresponds to the sensor position on the live image of the present frame. An initial sensor position on the reference image is set by being specified by the operator on the reference image. Second and subsequent sensor positions on the reference image are specified from the last sensor positions on the reference image in accordance with the displacement (direction and distance) of the sensor positions on the live images. The specification is repeated sequentially so as to identify a movement locus of the sensor position on the reference image.

The FFR value input unit 110a functions as an interface with the external FFR value measuring device 200a. The FFR value measuring device 200a measures an FFR value (myocardial portion fractional flow reserve) as an indicator indicating the blood flow rate. The degree of necessity of treatment is classified into three sections of "treatment necessary", "necessity judgment necessary", and "treatment unnecessary" in accordance with the degree of the FFR value. The FFR value measuring device 200a is constituted by the pressure sensor 210a and an FFR value calculator 211a. The FFR value is calculated based on a ratio of a pressure measurement value at each intravascular position relative to an aortic pressure serving as a reference. The pressure sensor 210a attached to the guide wire measures the pressure measurement value at each intravascular position. The FFR value calculator 211a calculates the FFR value by dividing the pressure measurement value at each intravascular position that is measured by the pressure sensor 210a by the aortic pressure measurement value that is measured by the pressure sensor 210a. Data of the FFR value is output in association with a code indicating a measurement time of the pressure measurement value at each intravascular position by the pressure sensor 210a.

The FFR value storage unit 111a stores therein pieces of data of a plurality of FFR values that are input through the FFR value input unit 110a. The pieces of data of the plurality of FFR values are related to the codes each of which indicates the measurement time of the pressure measurement value at each intravascular position by the pressure sensor 210a. The FFR value selector 32 selects an FFR value at the time same as a rising timing of the reference phase or the closest time thereto with reference to the measurement time code.

The mark generator 33 determines a mark having a color corresponding to the FFR value selected by the FFR value selector 32. The mark has a substantially rectangular shape having a width in accordance with a standard vascular diameter of a target blood vessel. The display controller 130a superimposes the mark generated by the mark generator 33 on the reference image stored in the X-ray image storage unit 22a cumulatively. The display unit 16a displays the reference image on which mark is superimposed cumulatively that is generated by the display controller 130a.

Figure 14:
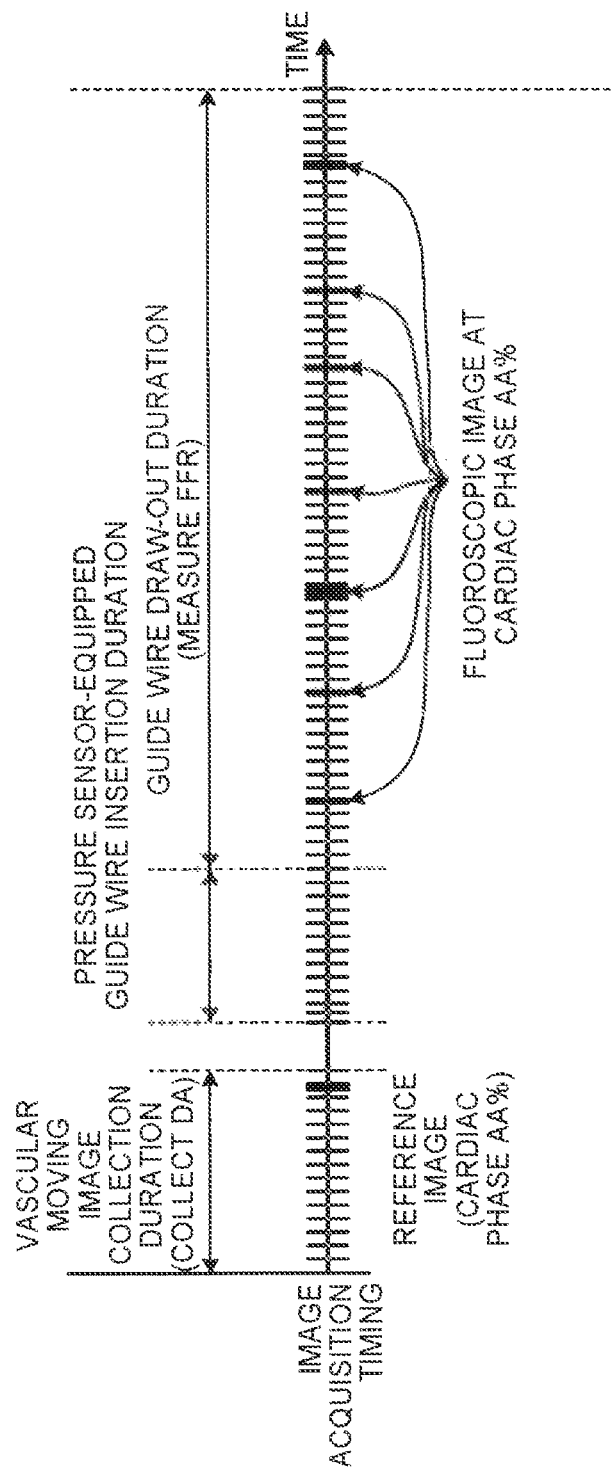
FIG. 14 is a view schematically illustrating a series of operations from collection of DA images to completion of draw-out of a guide wire in the embodiment.

FIG. 14 is a view illustrating fluoroscopy procedures in the embodiment together with procedures of insertion of the guide wire and injection of a contrast material. The schematic order of a series of operations according to the embodiment is as follows. (1) A vascular moving image is collected in a state in which the contrast material is injected through the catheter inserted into the blood vessel of the subject. The digital angiography (DA) is typically used as the X-ray acquiring technique in this case. (2) A frame on which an FFR target region of the subject is contrast-imaged most preferably among the DA images collected repeatedly in the procedure (1) is displayed on a reference monitor as a still image (reference image). (3) An FFR measurement target region is specified on the reference image in accordance with a direction from the operator. (4) The pressure sensor-equipped guide wire is inserted into a target site in the FFR measurement target region. (5) The measurement of the pressure (FFR value) is repeated through the pressure sensor while drawing the guide wire out. (6) The measured FFR values are color-coded in accordance with thresholds so as to be displayed on the reference image in the superimposed manner.

In a draw-out duration in the above-mentioned procedure (5), the FFR value measuring device 200a measures the FFR value repeatedly. Normally, the measurement cycle of the FFR value is a cycle shorter than a frame cycle in the X-ray fluoroscopy. Note that the placement duration and the draw-out duration may be continuous or may be separated temporally with interruption of the X-ray fluoroscopy.

Figure 15:
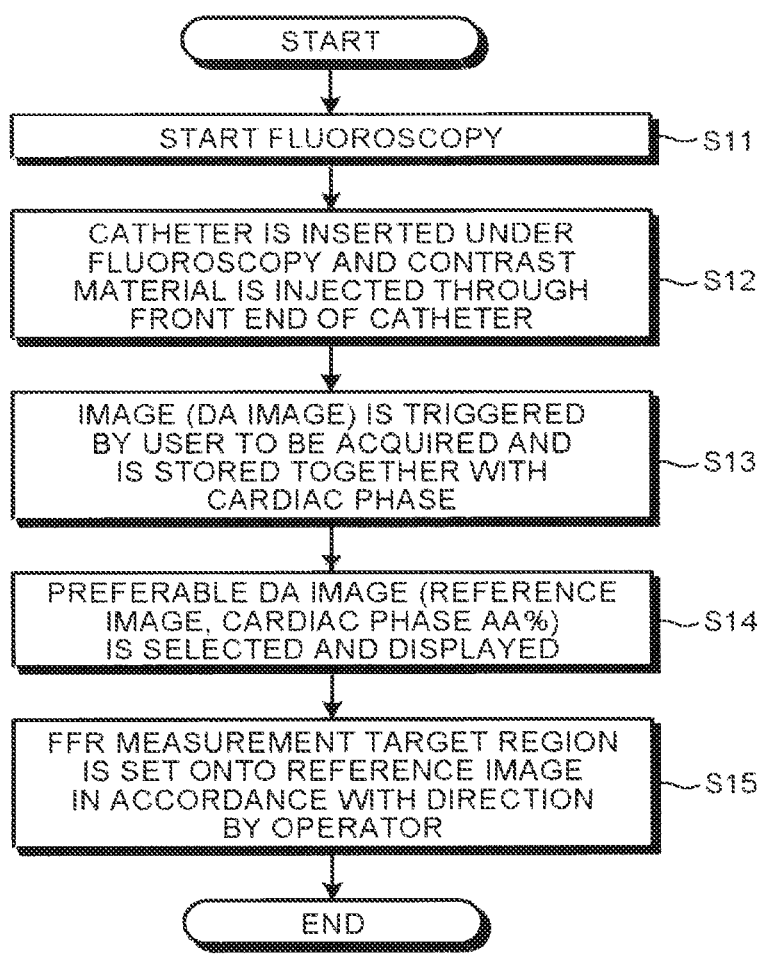
FIG. 15 is a flowchart illustrating processing procedures from insertion of a catheter in FIG. 14 to selection of a reference image.

FIG. 15 is a flowchart illustrating procedures from insertion of the catheter to completion of acquiring of the DA images. First, the mount unit 10a is moved to a position at which a desired vascular region of the subject can be observed with a direction from the operator through the input unit 21a and the X-ray fluoroscopic condition and the image collection condition are determined. Next, an X-ray fluoroscopic operation is started and a fluoroscopic image is collected under control of the controller 23a if the operator operates the mouse or the button as the input unit 21a (S11). As the X-ray fluoroscopic condition, an X-ray dose is lower than that of the X-ray acquiring for collecting a mask image and a contrast image, for example. The fluoroscopic image is displayed on the display unit 16a immediately.

The operator inserts the catheter to a target position under the X-ray fluoroscopy (S12). Next, a DA acquiring technique is selected and the DA acquiring is executed. In this case, a contrast material is injected through an injector synchronized with the X-ray diagnostic apparatus 100a, a contrast image is collected repeatedly, and a region on which the FFR should be measured is specified (S13). The DA image is obtained by high-dose pulse X rays, so that collection of the DA image is repeated several times at given timings normally. The data of each DA image is stored in the X-ray image storage unit 22a in association with a code indicating a DA image acquiring time and data of a cardiac phase of the subject at the time of the acquiring. It is noted that the data of the cardiac phase is supplied from an external electrocardiograph (not illustrated) connected to the X-ray diagnostic apparatus 100a.

Figure 16:
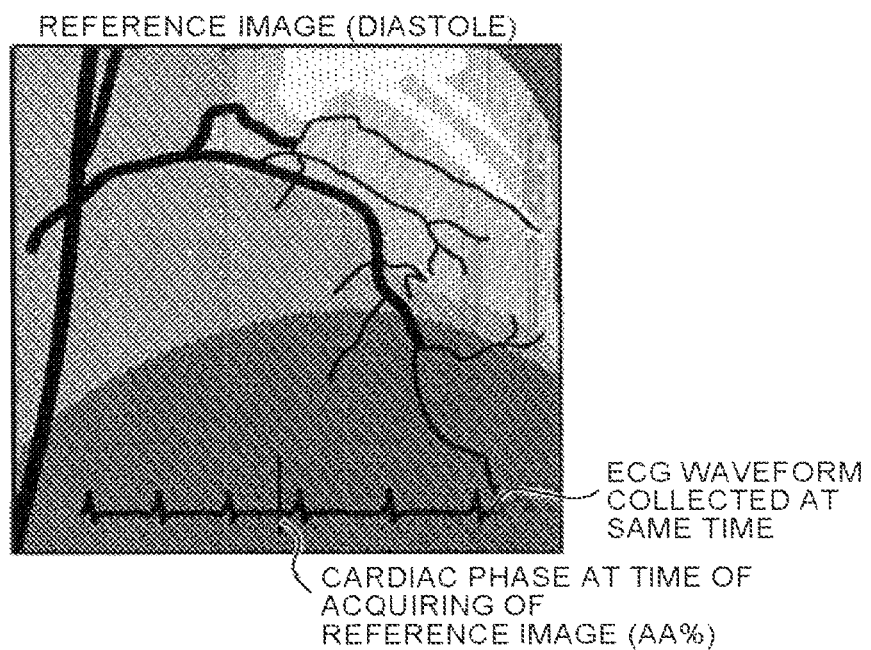
FIG. 16 is a view illustrating an example of the reference image selected in a process at S14 in FIG. 15.

A plurality of DA images are displayed as a list on the display unit 16a under control of the display controller 130a and one given DA image preferable for diagnosis of stenosis is selected as a reference image in accordance with a direction from the operator (S14). As illustrated in FIG. 16, description is made while the cardiac phase to which the reference image corresponds is assumed to be "AA %". The reference image may be selected based on the operator's standard. For example, an image having small noise or an image on which vascular region is located at the center may be selected. Alternatively, the X-ray diagnostic apparatus 100a may have a function of calculating brightness, noise and the like of an image and may select the reference image automatically.

Next, the operator operates the pressure sensor-equipped guide wire so as to move the pressure sensor 210a attached to the front end of the guide wire to a target position (position determined by the operator on the DA image) in the blood vessel and place it.

The operator operates the mouse on the reference image displayed on the display unit 16a in an enlarged manner so as to specify a position (initial position) of the pressure sensor 210a and the sensor initial position on the reference image is registered (S15). Data of the registered initial sensor position is stored in the X-ray image storage unit 22a together with data of the reference image. It is sufficient that the X-ray diagnostic apparatus 100a stores the registration position as coordinates based on a given point on the image or the reference image. The registration position may or may not be displayed on the reference image.

Figure 17:
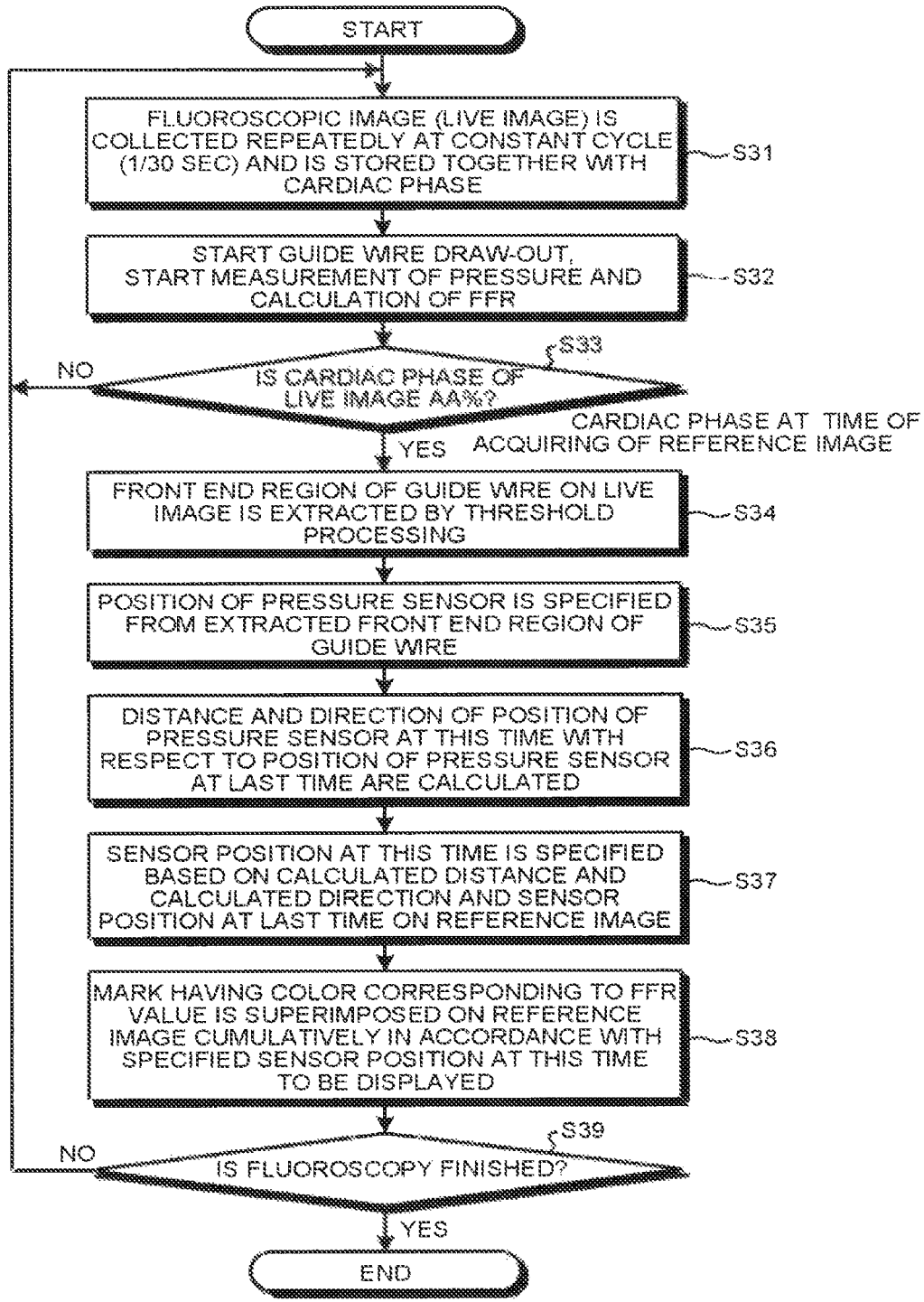
FIG. 17 is a flowchart illustrating processing procedures in a guide wire draw-out duration in FIG. 14.

FIG. 17 is a flowchart illustrating processing procedures in the draw-out duration of the guide wire in FIG. 14. The X-ray fluoroscopy is also executed by the controller 23a in the draw-out duration subsequent to the insertion duration (S31). With the execution of the X-ray fluoroscopy, a fluoroscopic image (live image) is generated repeatedly at a constant cycle. Each piece of data of the live image is stored in the X-ray image storage unit 22a in association with a code indicating the image generation time and data of the cardiac phase of the subject at the time of the image generation. In the draw-out duration, the pressure sensor 210a is moved in accordance with the draw-out operation of the guide wire from the placement position serving as a base point. The guide wire is drawn out gradually with the operation by the operator while the FFR value measuring device 200a measures the FFR value repeatedly in accordance with the output from the pressure sensor 210a (S32). The data of the FFR value is stored in the FFR value storage unit 111a in association with a code indicating the measurement time and data of the cardiac phase of the subject at the time of the measurement.

In the process at S33, the image processing controller 31 determines whether the cardiac phase is identical to the cardiac phase (AA %) of the reference image or in a range of ±5% of the cardiac phase (AA %) every time the live image is generated. Description is made by using the former case herein. The image processing controller 31 loads data of the live image generated at a timing identical to the cardiac phase (AA %) of the reference image from the X-ray image storage unit 22a and supplies it to the position specifying unit 120a. The position specifying unit 120a extracts the front end region of the guide wire from the supplied live image by the threshold processing (S34). The sensor position is specified from the extracted front end region (S35). The pressure sensor 210a is attached to a position distanced to the rear side from the front end of the guide wire by the distance L unique to the guide wire. For example, the sensor position is specified by correcting the above-mentioned distance L along the center axis of the guide wire from the extracted front end region of the guide wire.

Figure 18:
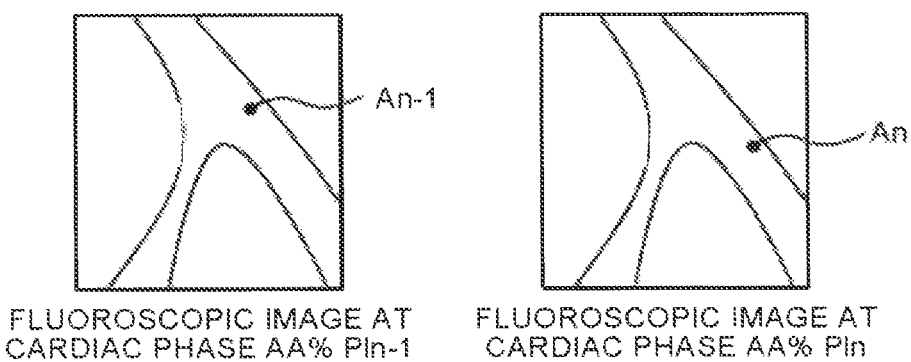
FIG. 18 is a descriptive view illustrating a process at S35 in FIG. 17.
Figure 19:
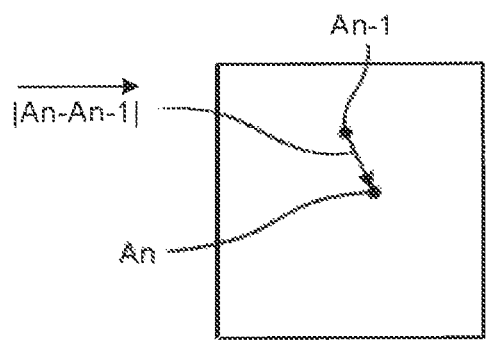
FIG. 19 is a descriptive view illustrating a process at S36 in FIG. 17.

As illustrated in FIG. 18 and FIG. 19, the position specifying unit 120a calculates the direction and the distance of a sensor position An specified on a live image PIn at this cardiac phase (AA %) with respect to a sensor position An−1 specified on a live image PIn−1 at the last cardiac phase (AA %) (S36).

Figure 20:
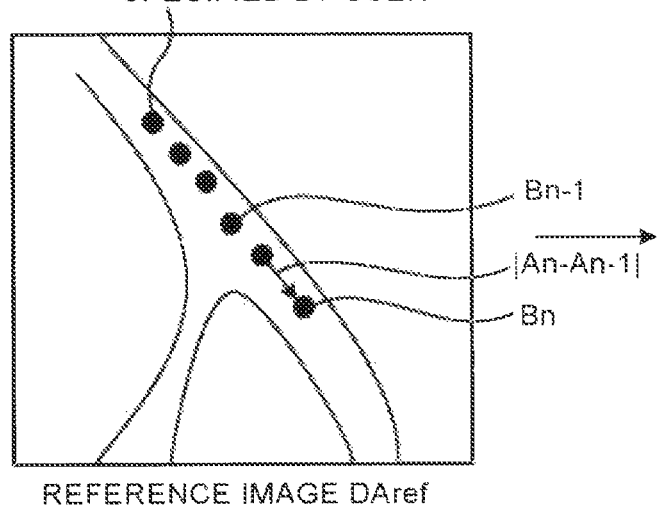
FIG. 20 is a descriptive view illustrating a process at S37 in FIG. 17.

Next, a sensor position on the reference image at this time is specified based on the calculated direction and the calculated distance and the last sensor position on the reference image (S37). That is to say, as illustrated in FIG. 20, a position after displacing a last sensor position Bn−1 on the reference image in accordance with the calculated direction and the calculated distance is specified as a present sensor position Bn on the reference image. It is noted that an initial sensor position B1 on the reference image is specified by the operator manually.

Thus, the sensor position on the reference image is specified from the sensor position on the reference image that has been specified at the last time based on the direction and the distance calculated from the last and present sensor positions specified on the live images continuously. This makes it possible to suppress expansion of deviation between the sensor position on the reference image and the sensor position on the live image. Main reasons of generation of the deviation include body motion of the subject itself due to temporal separation between acquiring of the reference image and generation of the live image and change of an anatomical position on the same site due to fluctuation of the cardiac cycle even at the same cardiac phase.

Next, a mark having a color in accordance with the FFR value measured at the time identical to the generation time of the live image processed at this time or the time closest thereto is superimposed on the sensor position specified at S37 on the reference image (S38). The FFR value is a value that is calculated based on a ratio of the pressure measurement value and the aortic pressure value. That is, the FFR value is given as a value from 0 to 1 normally. The FFR values from 0 to 1 are divided into a plurality of sections and a color phase is assigned to each section previously.

The processes at S31 to S38 are repeated through a process at S39 until the fluoroscopy is completed. The marks generated in sequence during the processes are superimposed on the reference image cumulatively.

Figure 21:
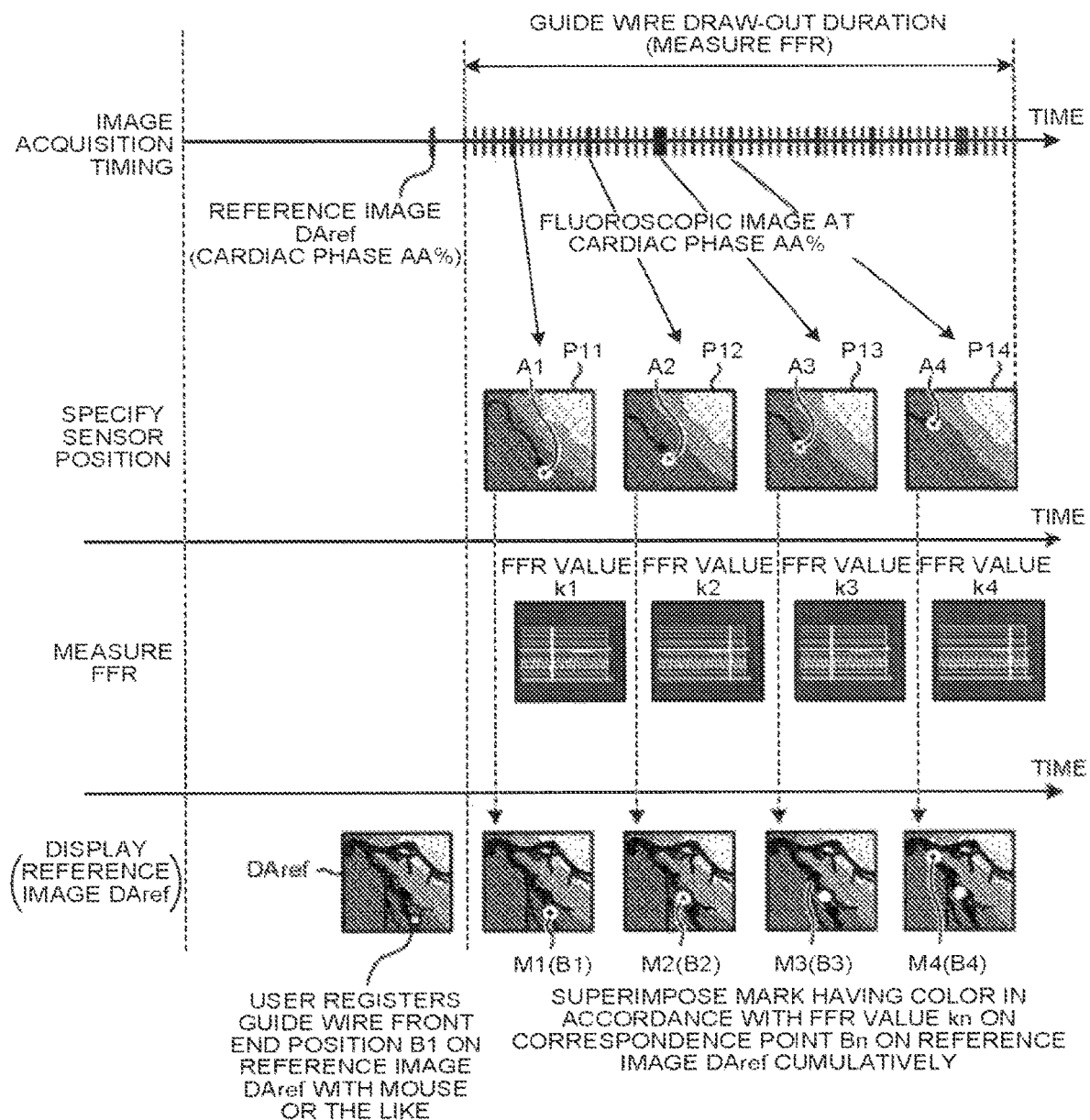
FIG. 21 is a descriptive view relating to a loop operation in processes at S31 to S38 in FIG. 17.
Figure 22:
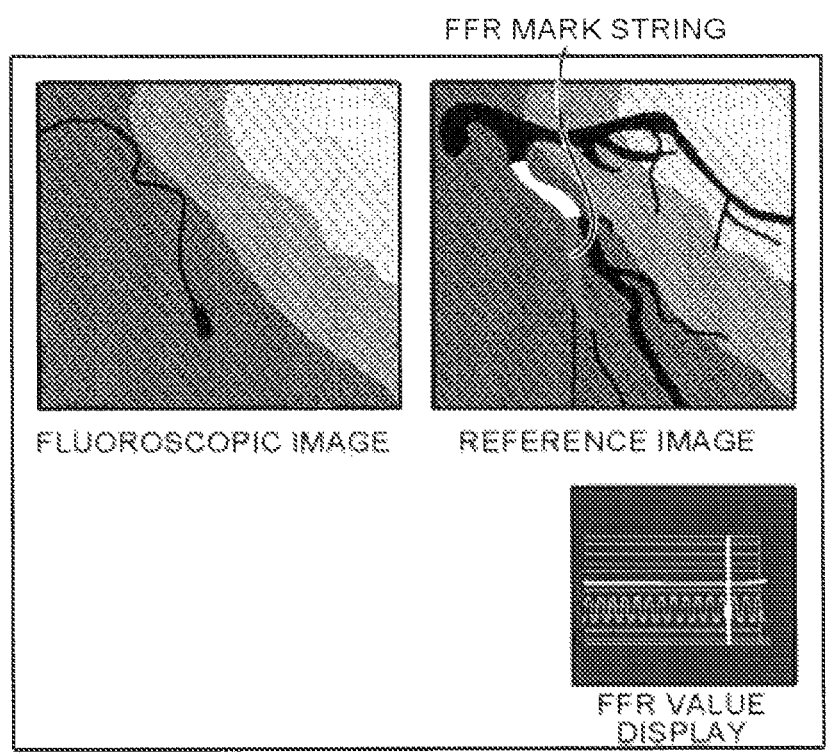
FIG. 22 is a view illustrating a display screen example of a display in the process at S38 in FIG. 17.

FIG. 21 illustrates a time chart indicating repeat of the processes at S31 to S38. A reference image DAref is displayed steadily in the draw-out duration and marks M1, M2, M3 . . . with colors in accordance with FFR values k1, k2, k3 . . . at the same phase AA % are superimposed on respective sensor positions B1, B2, B3 . . . cumulatively on the reference image DAref in accordance with the repeat of the cardiac cycle. As illustrated in FIG. 22, the reference image is displayed on the same screen together with the fluoroscopic image (live image) and the time chart of the FFR value.

As described above, with the use case, measurement positions of the indicator such as the FFR value effective for diagnosis of the vascular stenosis are capable of being checked on the reference image. This improves special visibility of the FFR value so as to enhance usability. That is to say, according to the embodiment, on the X-ray image relating to the subject into which the guide wire including the pressure sensor 210*a* is inserted, the FFR values can be displayed as marks on vascular sites at which pressures to be used for calculation of the FFR values are measured in the superimposed manner. This makes it possible to check the FFR values on the blood vessel instinctively, thereby expecting improvement of measurement accuracy of vascular stenosis portions by the operator. Furthermore, in the embodiment, the sensor position on the reference image is specified from the sensor position on the reference image that has been specified at the last time in accordance with the direction and the distance calculated from the last and present sensor positions specified on the live images continuously. This makes it possible to suppress expansion of deviation between the sensor position on the live image that is the actual FFR measurement position and the sensor position on the reference image that is displayed.

Figure 23:
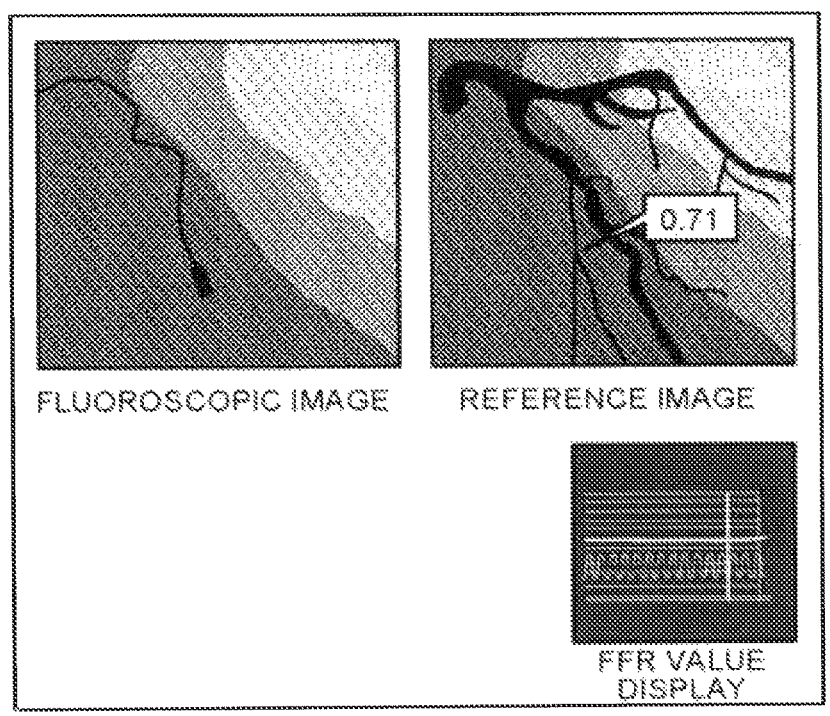
FIG. 23 is a view illustrating a display screen example in which a numerical value of an FFR value is superimposed on the reference image instead of a mark string on a display screen in FIG. 22.
Figure 24:
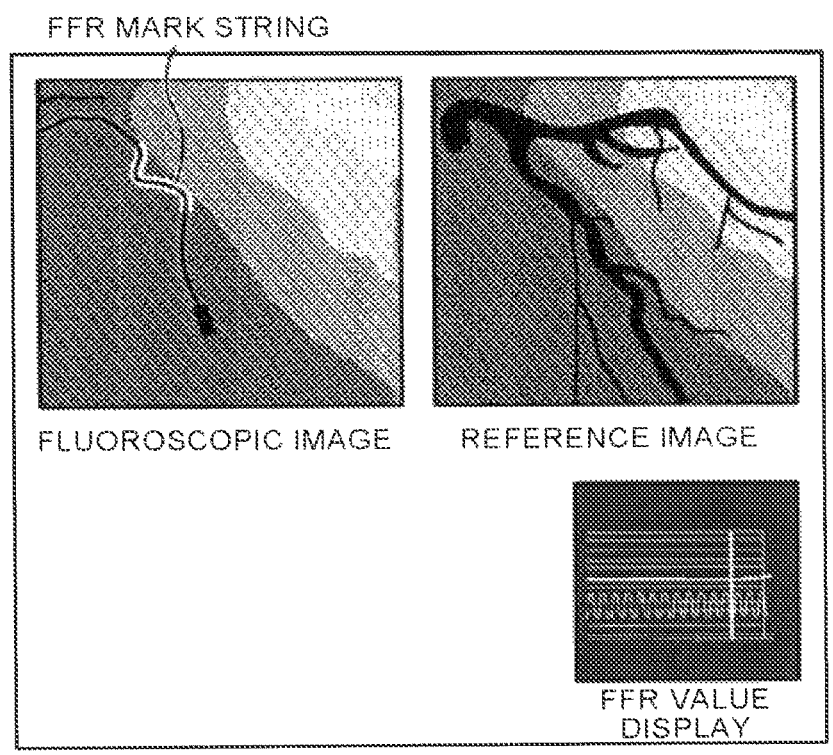
FIG. 24 is a view illustrating a display screen example in which the mark string is superimposed on a fluoroscopic image that has been switched from the display screen in FIG. 22.
Figure 25:
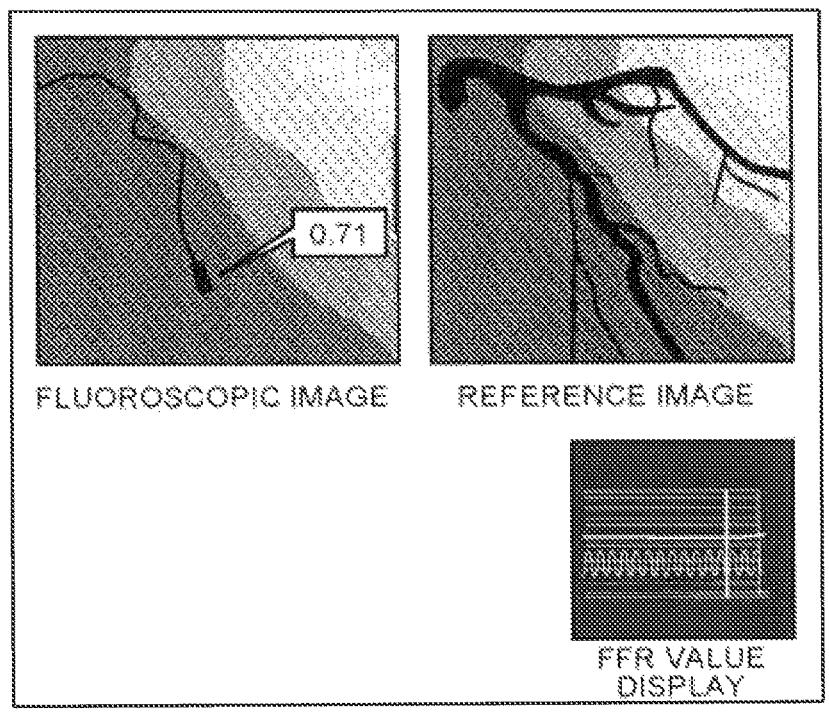
FIG. 25 is a view illustrating a display screen example in which the numerical value of the FFR value is superimposed on the fluoroscopic image instead of the mark string on the display screen in FIG. 22.
Figure 26:
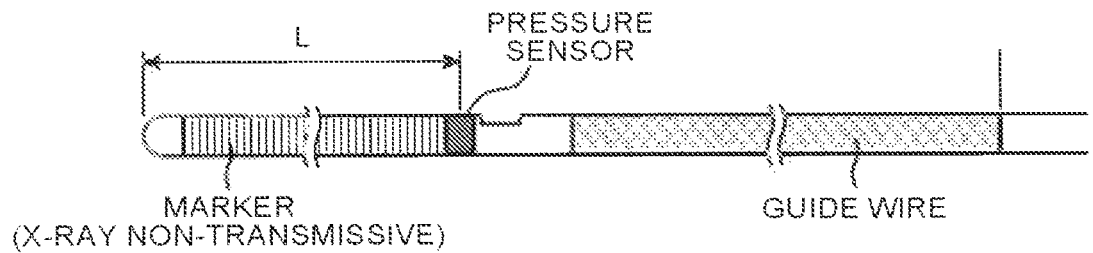
FIG. 26 is a side view of the guide wire.

A display mode of the FFR value on the reference image can be varied variously. For example, as illustrated in FIG. 23, when the operator operates the input unit 21*a* in a specific manner at a given timing during the measurement of the FFR value, a numerical value of the FFR value at that time may be displayed with a balloon at the sensor position on the reference image at that time. As illustrated in FIG. 24, a target on which the mark is to be displayed in a superimposed manner may be made to be capable of being switched from the reference image to the live image (fluoroscopic image). In addition, as illustrated in FIG. 25, a numerical value of the FFR value may be made to be capable of being switched from the reference image to the live image (fluoroscopic image) so as to be displayed in the superimposed manner.

Although the fluoroscopic image is collected repeatedly at a constant cycle such as 1/30 sec while X rays are emitted intermittently in the above-mentioned embodiments, the embodiment is not limited thereto. The fluoroscopic image may be collected while the X rays are emitted at a constant time interval. In such a case, while the operator operates to draw out the guide wire gradually, the fluoroscopic image is collected at a constant time interval. Then, the display controller 130*a* displays marks at sensor positions at which fluoroscopic images are collected on the reference image or the fluoroscopic images. The FFR value measuring device 200*a* may execute measurement of the FFR value repeatedly in accordance with the output of the pressure sensor 210*a* or may execute at a timing of the fluoroscopic image. This makes possible to reduce an exposure dosage of the subject.

Fourth Embodiment

Figure 27:
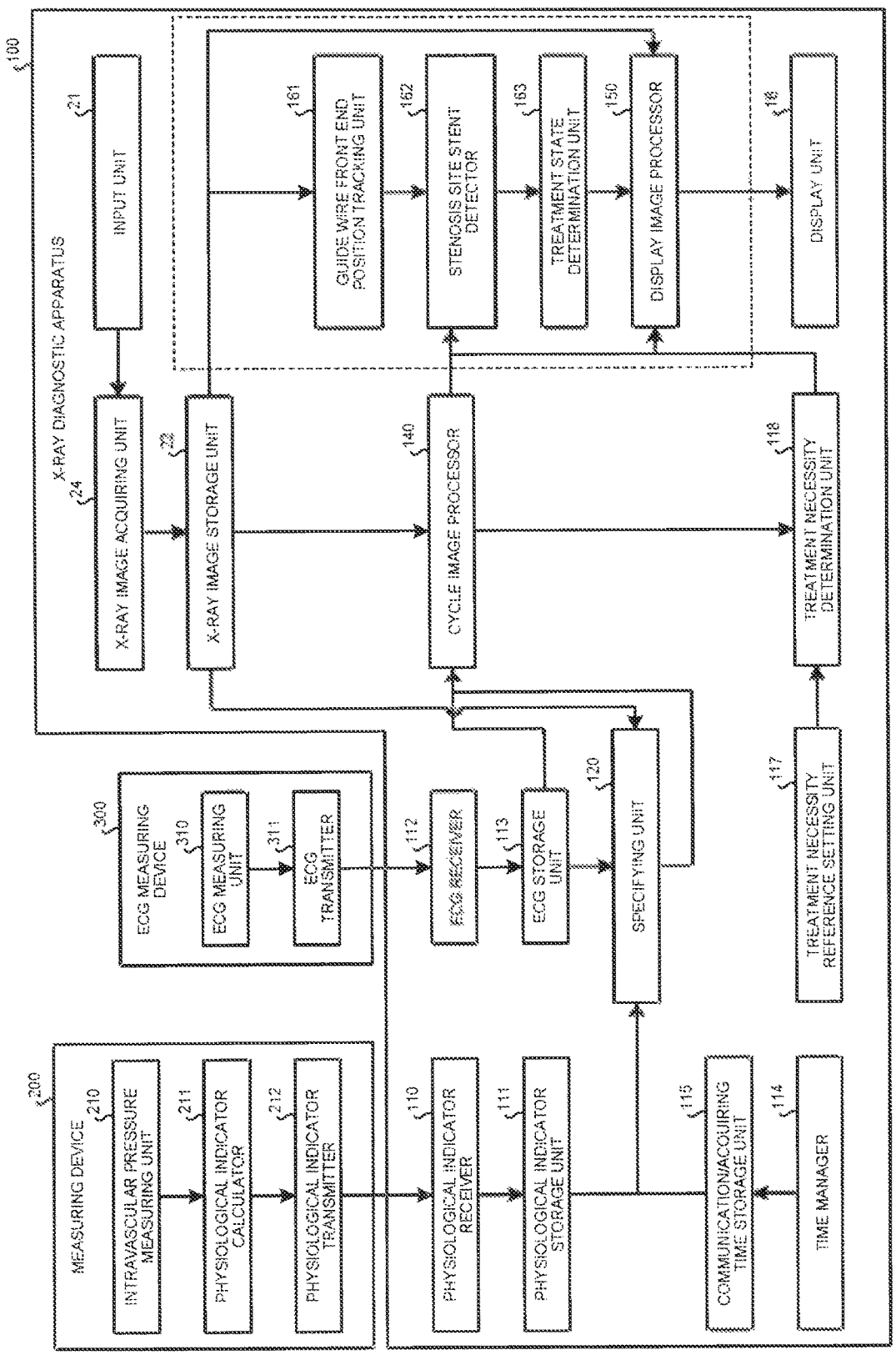
FIG. 27 is a block diagram illustrating a configuration of an X-ray diagnostic apparatus in a fourth embodiment.

In a fourth embodiment, a treatment state is further displayed. FIG. 27 is a block diagram illustrating a configuration of an X-ray diagnostic apparatus 100 according to the fourth embodiment. As illustrated in FIG. 27, the X-ray diagnostic apparatus 100 according to the fourth embodiment further includes respective parts for displaying and updating a treatment state in real time.

A guide wire front end position tracking unit 161 specifies a front end position of the guide wire in real time in an X-ray image acquired in real time. The front end position of the guide wire is capable of being specified by using an existing known technique as in the intravascular pressure measurement position specifying unit 122.

A stenosis site stent detector 162 extracts a treating tool for the stenosis site, such as a stent and a balloon, in the X-ray image. The stenosis site stent detector 162, for example, performs image analysis based on the front end position of the guide wire that is specified by the guide wire front end position tracking unit 161 so as to extract the treating tool. The treating tool is capable of being extracted by using an existing known technique as in the intravascular pressure measurement position specifying unit 122. Note that the treating tool needs to be extracted after the shape of the treating tool is checked.

A treatment state determination unit 163 determines a treatment state based on whether the treating tool is placed on the stenosis site on the image. The treatment state determination unit 163, for example, determines that treatment is done when the treating tool is determined to be placed as a result of detection by the stenosis site stent detector 162. On the other hand, the treatment state determination unit 163 determines that treatment is not done when the treating tool is determined not to be placed.

Figure 28:
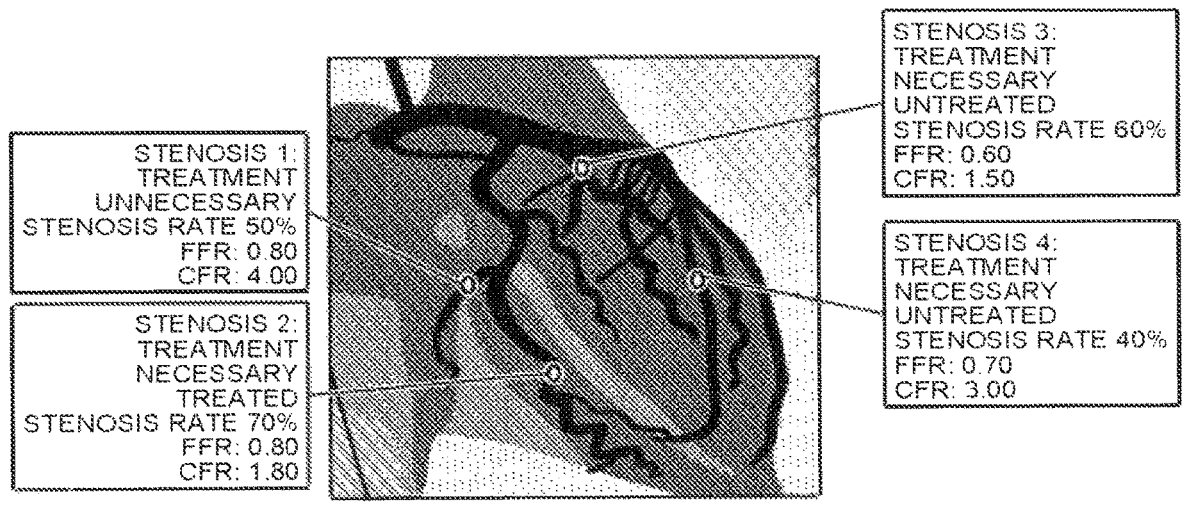
FIG. 28 is a view illustrating a display example in the fourth embodiment.

FIG. 28 is a view illustrating a display example in the fourth embodiment. In the fourth embodiment, as illustrated in FIG. 28, the display controller 130 further displays information ("treated" and "untreated") indicating the treatment state in accordance with a determination result by the treatment state determination unit 163.

Fifth Embodiment

Figure 29:
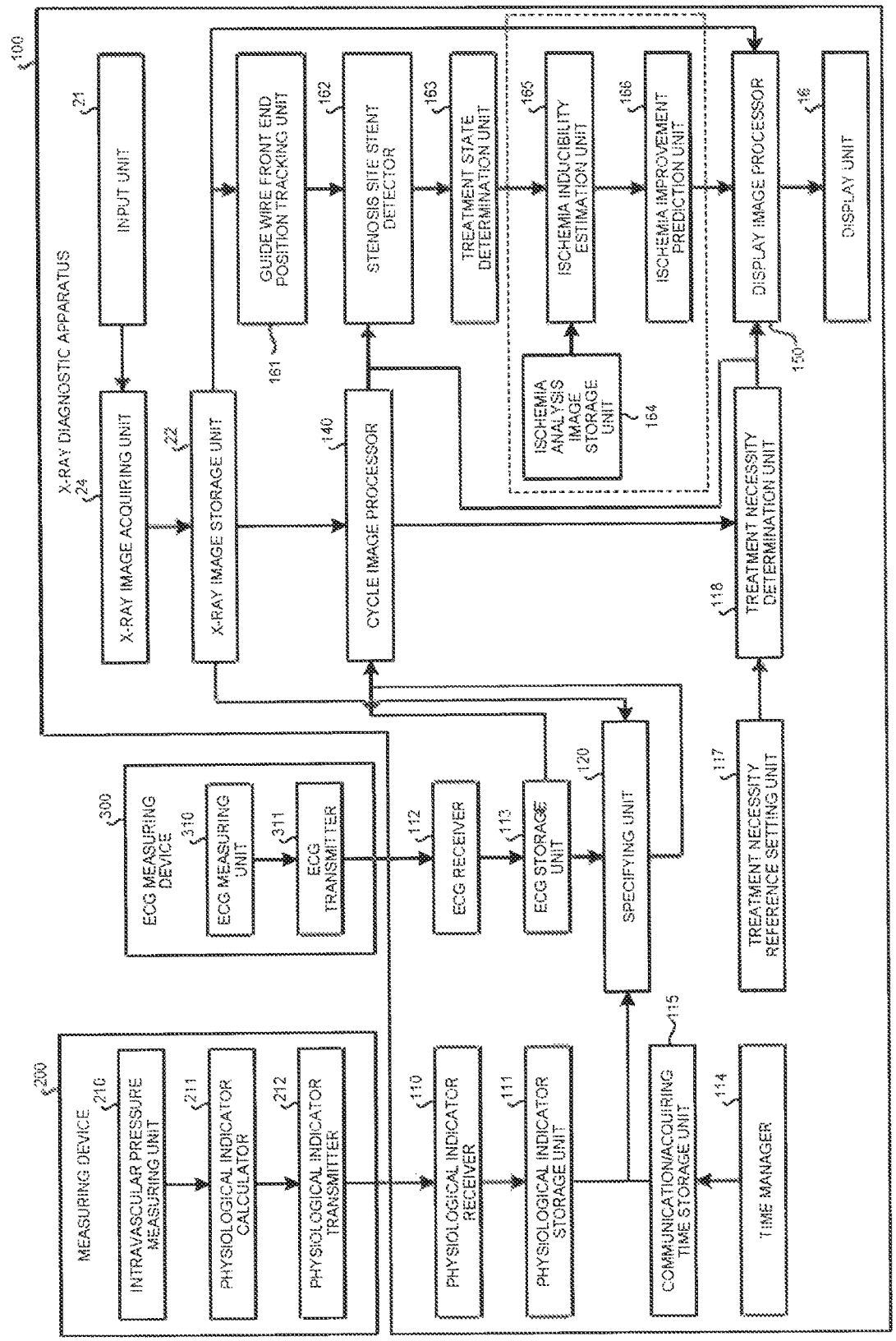
FIG. 29 is a diagram illustrating configurations of an X-ray diagnostic apparatus, a measuring device, and an ECG measuring device in a fifth embodiment.

In a fifth embodiment, information of myocardial ischemia improvement prediction with treatment is further displayed. FIG. 29 is a diagram illustrating configurations of an X-ray diagnostic apparatus 100, a measuring device 200, and an ECG measuring device 300 according to the fifth embodiment. As illustrated in FIG. 29, the X-ray diagnostic apparatus 100 according to the fifth embodiment further includes the respective parts for predicting improvement of the myocardial ischemia in real time with treatment of the stenosis site and displaying a prediction result.

An ischemia analysis image storage unit 164 stores therein an ischemia analysis result image such as myocardial perfusion. The ischemia analysis result image is, for example, a computed tomography (CT) image, a combined image of the CT image and a single photon emission computed tomography (SPECT) image, or the like, and is an image acquired by an X-ray CT apparatus or an SPECT apparatus. In the fifth embodiment, it is assumed that positioning between the X-ray image acquired by the X-ray diagnostic apparatus 100 and the ischemia analysis result image stored in the ischemia analysis image storage unit 164 is already completed. The positioning is capable of being performed by using an existing known technique. For example, the positioning is capable of being performed based on information such as acquiring conditions including as an angle of the C arm 13, brightness distribution of a Ray-Sum image (sum value projected image), and shapes of heat and coronary artery.

An ischemia inducibility estimation unit 165 estimates an ischemia inducibility indicating the degree that ischemia is induced by stenosis. For example, known is a relation between coronary arteries and myocardial regions that are innervated by the coronary arteries anatomically. The ischemia inducibility estimation unit 165 calculates the ischemia inducibility (for example, induction rate) at each position in the ischemic myocardium based on the relation between the FFR of the stenosis on the coronary artery that innervates an myocardial region and a range and the degree of ischemia on the myocardial region.

The FFR is information received from the measuring device 200 and the range and degree of the ischemia are pieces of information obtained from the ischemia analysis result image. For example, it is sufficient that the ischemia inducibility estimation unit 165 calculates the induction rate by weighing a plurality of FFRs when a plurality of stenosis sites is present on one coronary artery. The ischemia inducibility estimation unit 165 previously learns an algorithm of calculating the ischemia inducibility based on the relation between the FFR and the range and degree of the ischemia and inputs these pieces of information to the algorithm so as to calculate the ischemia inducibility.

An ischemia improvement prediction unit 166 predicts improvement of the myocardial ischemia with the treatment of the stenosis site in real time by using the ischemia inducibility estimated by the ischemia inducibility estimation unit 165. In the case of multivessel lesion and multiple lesions, treatment is performed in the order from a stenosis site having a higher ischemia inducibility. The treatment does not achieve expected improvement of the ischemia in some cases. In the fifth embodiment, in order to evaluate the treatment result during the treatment, the FFR is measured and the ischemia inducibility estimation unit 165 calculates the ischemia inducibility again by using the measured FFR again every time the stenosis site is treated.

The ischemia improvement prediction unit 166 obtains a difference between the ischemia inducibility calculated before the treatment and the ischemia inducibility calculated after the treatment for each position in the ischemic myocardium so as to predict improvement of the myocardial ischemia at each position in the ischemic myocardium. Furthermore, the display controller 130 further displays the ischemia analysis result image together with the X-ray image, and displays a prediction result (that is, predicted degree of improvement) on the ischemia analysis result image.

Figure 30:
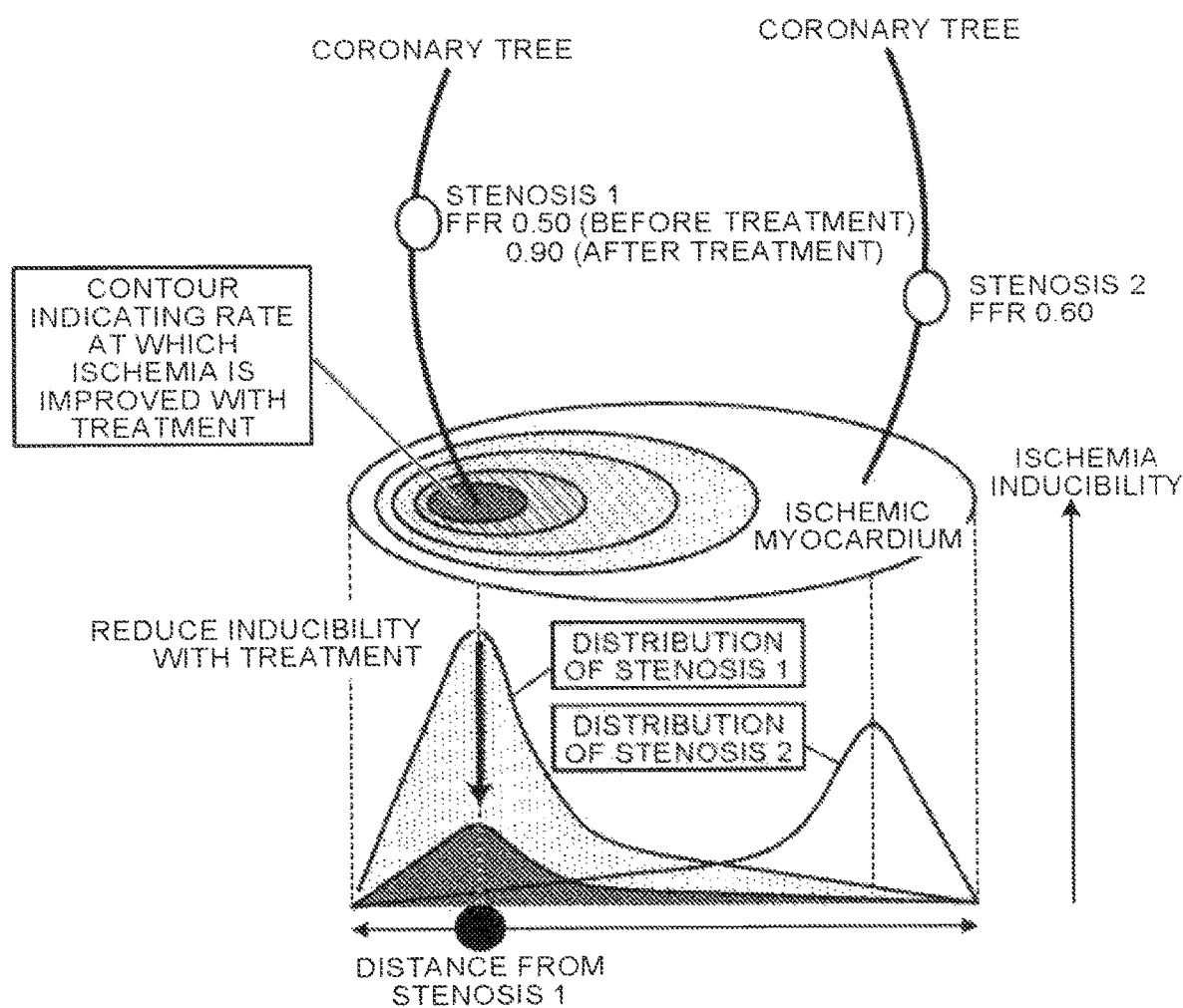
FIG. 30 is a view for explaining myocardial ischemia improvement prediction in the fifth embodiment.

FIG. 30 is a view for explaining myocardial ischemia improvement prediction in the fifth embodiment. A graph of a signal value as illustrated in FIG. 30 indicates a signal value as an ischemia analysis result of myocardial perfusion or the like. The signal value is analyzed from parameters such as a time to peak (TTP), a myocardial blood volume (MBV), and a mean transit time (MTT). As illustrated in FIG. 30, for example, the display controller 130 displays a contour indicating a rate of improvement of ischemia when the FFR is changed from "0.50" to "0.90" with the treatment of stenosis 1.

Figure 31:
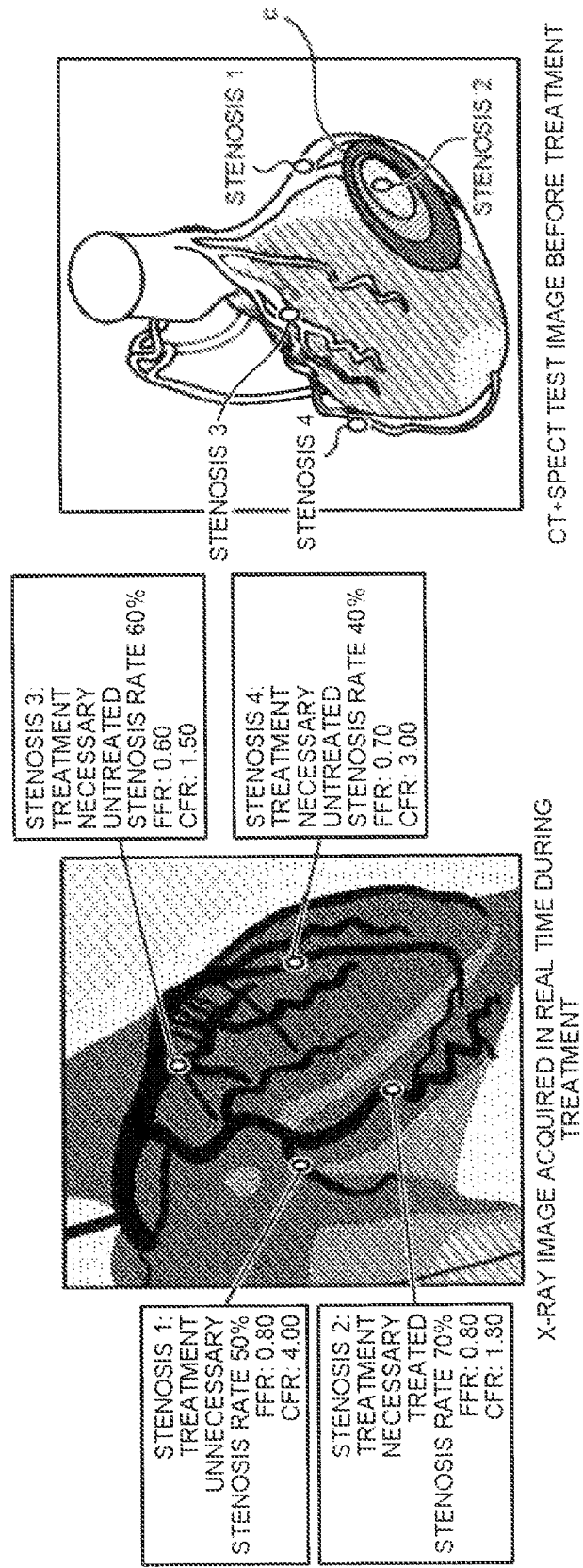
FIG. 31 is a view illustrating a display example in the fifth embodiment.

FIG. 31 is a view illustrating a display example in the fifth embodiment. In the fifth embodiment, as illustrated in FIG. 31, for example, the ischemia analysis result image in addition to the X-ray image on which measurement data and the like are displayed in the superimposed manner is also displayed on the display unit 16. Then, as illustrated in FIG. 31, the display controller 130 displays a contour c on the ischemia analysis result image before treatment, for example. In the fifth embodiment, the contour c is formed by drawing lines for segmentation in accordance with the difference of the inducibility between before and after the treatment. For example, it is sufficient that the display controller 130 assigns dark color when the difference of the inducibility between before and after the treatment is large, and the display controller 130 assigns light color when the difference between before and after the treatment is small. Furthermore, the embodiment is not necessarily limited to the contour and the ischemia analysis result image may be displayed while changing colors on a pixel basis, for example.

If the prediction of improvement is displayed on the ischemia analysis result image in this manner, a person involved in the treatment is capable of checking the range and the degree of improvement of ischemia visually. It is difficult to perform a complicated screen operation during the catheter procedures, so that efficient evaluation can be made with the above-mentioned display. If the FFR becomes a high value with the treatment of the stenosis site, for example, the range and the degree of the myocardial ischemia to which the stenosis site relates is indicated to be improved.

Other Embodiments

The embodiments are not limited to the above-mentioned embodiments and can be executed in various types of other different modes.

Although a measured indicator is used as the indicator relating to the blood flow in the above-mentioned embodiment, the embodiment is not limited thereto. For example, a simulation indicator such as a CT-FFR may be used as the indicator. FIG. 32 is a view illustrating generation of a display image and a display example in another embodiment. For example, as illustrated in FIG. 32, the controller 23 in the X-ray diagnostic apparatus 100 generates a three-dimensional vascular model based on CT volume data at the time of initial diagnose. Then, the controller 23 calculates an FFR value at each position on the generated three-dimensional vascular model. It is noted that the FFR value at each position on the generated three-dimensional vascular model is capable of being calculated by an existing known technique.

As illustrated in FIG. 32, on the X-ray image (contrast image or non-contrast image) of the same subject of which CT volume data is collected, the display controller 130 displays a calculation position of the FFR value calculated by the controller 23 and the calculated FFR value (CT-FFR: 0.7 in FIG. 32) in association with the calculation position. In the X-ray diagnostic apparatus in the application, processing can be performed on four-dimensional data. That is to say, the controller 23 generates a three-dimensional vascular model from each piece of CT volume data over time so as to calculate the FFR value at each position.

Then, the display controller 130 specifies volume data corresponding to a time phase of each X-ray image of a series of X-ray images (contrast images or non-contrast images) collected continuously by using the ECG and displays the FFR value calculated by using the specified volume data in association with the calculation position on the X-ray image. This enables an operator to grasp the FFR value at each position at a time phase of each of the plurality of X-ray images before measurement. As illustrated in FIG. 32, when various types of indicators are measured actually for treatment, the display controller 130 displays the measured value "FFR: 0.8 and CFR: 4.00" and the simulation result "CT-FFR: 0.7" at the time of diagnosis at the same time. This makes it possible to compare the simulation value and the measured value relatively easily, thereby performing subsequent diagnosis efficiently.

Although the X-ray diagnostic apparatus 100 has been described as an example of the medical image diagnostic apparatus in the above-mentioned embodiment, the embodiment is not limited thereto. The embodiment is capable of being applied to other medical image diagnostic apparatuses such as an ultrasound diagnosis apparatus, a magnetic resonance imaging apparatus, and a nuclear medicine imaging apparatus in the same manner. Furthermore, the embodiment may be applied to image processing apparatuses different from the medical image diagnostic apparatuses. In this case, for example, the image processing apparatus receives various pieces of information from a measuring device or a medical image diagnostic apparatus, or receives input from an operator, and performs the same pieces of processing as those performed by the above-mentioned specifying unit 120 and display controller 130 by using these pieces of information. Note that the image processing apparatuses are various types of apparatus such as a workstation, an image server and a viewer for a picture archiving and communication system (PACS), and an electronic chart system.

Furthermore, the embodiment may be applied to a measuring device (blood pressure monitor) different from the medical image diagnostic apparatuses and the image processing apparatuses. In such a case, the measurement device has a monitor for image display, for example. The measuring device receives various pieces of information from the medical image diagnostic apparatus or receives input from an operator, and performs the same pieces of processing as those performed by the above-mentioned specifying unit 120 and display controller 130 by using these pieces of information. As the blood pressure monitor, a central peripheral vein blood pressure monitor and the like are included.

Furthermore, the embodiment is not limited to the above-mentioned embodiments and various types of following modes can be combined appropriately. First, examples of the modes of the linkage with acquiring of a display image include not only modes of linkage in real time (display the measurement position on the image that is being acquired) and linkage off-line (display the measurement position on the image collected previously) but also a mode of linkage with an image stored in another apparatus (for example, workstation). Furthermore, examples of the display image include not only the 2D image and the time-series 2D image but also a 3D image and a 4D image. Examples of the display image include not only the contrast image and the non-contrast image but also an image that is being contrast-imaged (including an image that is not contrast-imaged completely). Examples of a processing target image include not only the X-ray image but also a CT image, a SPECT image, and an image collected by another medical image diagnostic apparatus. As the method of determining the treatment state, there are a method of detecting change of an intravascular pressure and a method of making an operator input the treatment state in addition to the above-mentioned image analysis. Furthermore, as the method of making temporal synchronization between various pieces of information received from the measuring device 200 and the like and the X-ray image, there are a method of making synchronization at each time simply, a method of making synchronization by extracting the time around the time at which internal pressure around the stenosis is measured only without setting all the times at which pieces of data are stored as synchronization targets, and the like.

Furthermore, although the FFR and the CFR have been described as indicators relating to the blood flow in the above-mentioned embodiment, the embodiment is not limited thereto. For example, other indicators obtained by customizing them may be targeted.

Although the acquiring direction of the C arm is fixed in the above-mentioned embodiment, the embodiment is not limited thereto. It is sufficient that the above-mentioned various pieces of processing are performed again in accordance with the change of the acquiring direction of the C arm.

Although the coronary artery is supposed in the above-mentioned embodiment, the embodiment is not limited thereto.

The embodiment is capable of being applied to other blood vessels in the same manner.

With the image processing apparatus, the medical image diagnostic apparatus, and the blood pressure monitor according to at least one of the above-mentioned embodiments, a measurement position serving as a physiological indicator is capable of being grasped on the vascular image.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to
determine a plurality of locations of a pressure sensor that is inserted into a subject from each of a plurality of X-ray fluoroscopic images acquired sequentially,
determine a plurality of reference positions on a contrast X-ray image of the subject that correspond to the plurality of locations of the pressure sensor, and
cause a display to display the contrast X-ray image indicating one of a plurality of values derived from output of the pressure sensor, and to display a chart based on the plurality of values,
wherein the plurality of values are values related to blood flow.

2. The image processing apparatus according to claim 1, further comprising:
an input interface configured to accept an operation to input a position where the displayed value was obtained.

3. The image processing apparatus according to claim 1, wherein, when an instruction to indicate a value on the contrast X-ray image is received from a user, the processing circuitry is configured to cause the display to display the contrast X-ray image indicating one of the plurality of values, and to display the chart and a fluoroscopic image acquired after the plurality of X-ray fluoroscopic images.

4. The image processing apparatus according to claim 3, wherein the chart indicating the plurality of values is generated from output of the pressure sensor during acquisition of the plurality of X-ray fluoroscopic images.

5. The image processing apparatus according to claim 1, wherein the processing circuitry is configured to superimpose a line segment at a position corresponding to the displayed value in the chart based on the plurality of values.

6. The image processing apparatus according to claim 1, wherein the processing circuitry is configured to cause the display to display the contrast X-ray image on which the displayed value is indicated at a position near the position where the displayed value was obtained in the contrast X-ray image.

7. The image processing apparatus according to claim 1, wherein the processing circuitry is configured to determine the plurality of reference positions on a contrast X-ray image based on a front end of the pressure sensor drawn on the plurality of X-ray fluoroscopic images.

8. The image processing apparatus according to claim 1, wherein the processing circuitry is further configured to
collect the plurality of X-ray fluoroscopic images acquired by an X-ray diagnostic apparatus,
collect the plurality of values measured by a measuring device, and
associate acquisition phases of the plurality of X-ray fluoroscopic images with measurement phases of the plurality of values.

9. An X-ray diagnostic apparatus comprising:
processing circuitry configured to
acquire a contrast X-ray image of a subject and sequentially acquire a plurality of X-ray fluoroscopic images of the subject,
determine a plurality of locations of a pressure sensor that is inserted into the subject from each of the plurality of X-ray fluoroscopic images,
determine a plurality of reference positions on the contrast X-ray image of the subject that correspond to the plurality of locations of the pressure sensor, and
cause a display to display the contrast X-ray image indicating one of a plurality of values derived from output of the pressure sensor, and to display a chart based on the plurality of values,
wherein the plurality of values are values related to blood flow.

10. The X-ray diagnostic apparatus according to claim 9, wherein the processing circuitry is configured to acquire the plurality of X-ray fluoroscopic images while the pressure sensor is drawn out.

11. An image processing method comprising:
determining a plurality of locations of a pressure sensor that is inserted into a subject from each of a plurality of X-ray fluoroscopic images acquired sequentially;
determining a plurality of reference positions on a contrast X-ray image of the subject that correspond to the plurality of locations of the pressure sensor; and
causing a display to display the contrast X-ray image indicating one of a plurality of values derived from output of the pressure sensor, and to display a chart based on the plurality of values,
wherein the plurality of values are values related to blood flow.

* * * * *